(12) United States Patent
Colloredo-Mansfeld et al.

(10) Patent No.: US 12,171,681 B2
(45) Date of Patent: Dec. 24, 2024

(54) USING SENSORS TO DETECT MOVEMENT AND USE OF BRACES

(71) Applicant: MiracleFeet, Chapel Hill, NC (US)

(72) Inventors: Francesca Nancy Rachel Colloredo-Mansfeld, Chapel Hill, NC (US); Christopher Jonathan George Ferris, Ickleton (GB); Thomas Matthew Watts, Ickleton (GB)

(73) Assignee: MiracleFeet, Chapel Hill, NC (US)

( * ) Notice: Subject to any disclaimer, the term of this patent is extended or adjusted under 35 U.S.C. 154(b) by 951 days.

(21) Appl. No.: 17/138,115

(22) Filed: Dec. 30, 2020

(65) Prior Publication Data

US 2021/0196499 A1    Jul. 1, 2021

Related U.S. Application Data

(60) Provisional application No. 62/954,822, filed on Dec. 30, 2019.

(51) Int. Cl.
| | | |
|---|---|---|
| *A61F 5/01* | (2006.01) | |
| *A61B 5/11* | (2006.01) | |
| *G01C 21/10* | (2006.01) | |
| *G01C 19/00* | (2013.01) | |

(52) U.S. Cl.
CPC ............. *A61F 5/0116* (2013.01); *A61B 5/11* (2013.01); *G01C 21/10* (2013.01); *A61B 2562/0219* (2013.01); *A61H 2201/5058* (2013.01); *A61H 2201/5084* (2013.01); *G01C 19/00* (2013.01)

(58) Field of Classification Search
CPC ....... A61F 5/0116; G01C 19/00; G01C 21/10; A61B 2562/0219; A61B 5/11; A61H 2201/5058; A61H 2201/5084
See application file for complete search history.

(56) References Cited

U.S. PATENT DOCUMENTS

| | | | |
|---|---|---|---|
| 2007/0088240 A1* | 4/2007 | Dobbs | A61F 5/0193 602/5 |
| 2014/0094728 A1 | 4/2014 | Sodorberg et al. | |
| 2014/0257156 A1 | 9/2014 | Capra et al. | |
| 2018/0318121 A1 | 11/2018 | Mitchell | |
| 2019/0021894 A1 | 1/2019 | Zelen et al. | |

(Continued)

FOREIGN PATENT DOCUMENTS

EP    1464281 A1    10/2004

OTHER PUBLICATIONS

Lee Yhoung, PCT International Search Report, Mar. 23, 2021, 2 pages, US as receiving office.

(Continued)

*Primary Examiner* — Eric J Messersmith
(74) *Attorney, Agent, or Firm* — Smith & Woldesenbet Law Group, PLLC

(57) ABSTRACT

A brace that includes a body and a sensor device disposed in the body, where the sensor device includes a sensor that is configured to measure at least one parameter associated with a position of the housing. The brace also includes a controller communicably coupled to the sensor device. The controller can be configured to receive a plurality of measurements of the at least one parameter taken by the sensor device. The controller can also be configured to evaluate each measurement of the plurality of measurements.

20 Claims, 12 Drawing Sheets

(56) References Cited

U.S. PATENT DOCUMENTS

2019/0167988 A1    6/2019  Shahriari et al.
2020/0054474 A1*  2/2020  Ramos .................... A63F 13/80
2020/0237291 A1*  7/2020  Sundaram ................ A61B 5/11

OTHER PUBLICATIONS

Lee Yhoung, Written Opinion of the International Searching Authority, Mar. 23, 2021, 5 pages, US as receiving office.
Lee Young, International Search Report and Written Opinion issued in application PCT/US2020/067488, completion date Feb. 28, 2021, mailing date Mar. 23, 2021, 7 pages, Mail Stop PCT, Attn: ISA/US, Commissioner for Patents, P.O. Box 1450, Alexandria, Virginia, 22313-1450 U.S.A.

* cited by examiner

USING SENSORS TO DETECT MOVEMENT AND USE OF BRACES

CROSS-REFERENCE TO RELATED APPLICATIONS

This application claims priority under 35 U.S.C. § 119 to U.S. Provisional Patent Application Ser. No. 62/954,822, titled "Using Sensors To Detect Movement and Use of Braces" and filed on Dec. 30, 2019. The entire contents of these aforementioned applications are hereby incorporated herein by reference.

TECHNICAL FIELD

The present disclosure relates generally to orthopedic braces, and more particularly to systems, methods, and devices for detecting movement and use of braces, such as foot abduction braces.

BACKGROUND

Clubfoot, also known as talipes equinovarus, is a congenital birth defect that causes one or both feet to turn inward and/or downward. The exact causes of clubfoot are unknown, but research indicates genetic factors may play a role. Clubfoot results from abnormal development of the muscles, tendons, and bones of the fetus. Shortened tendons and ligaments on the inside of the lower leg lead to the foot turning inward. A tight Achilles tendon contributes to rigidity of the foot.

Clubfoot occurs in approximately 1 out of 800 births, with some variation across countries and ethnic groups and with an increased incidence in children born to a parent with clubfoot. Clubfoot occurs more often in boys than girls. There are about 175,000 new cases of clubfoot each year around the world. For children born with clubfoot, both feet are affected in about 50% of the cases. Without treatment, children born with clubfoot cannot walk properly, and the untreated condition can lead to severe disability. Treatment can include the use of braces, casts, and/or surgery. Non-surgical treatment of clubfoot has gained popularity in recent years and consists of a series of leg castings, followed by use of a foot abduction brace for several years. Similarly, for other abnormal conditions (e.g., scoliosis, sprains, fractures) of one or more parts of the human body, braces can be used to manage or correct such abnormal conditions.

SUMMARY

In general, in one aspect, the disclosure relates to a brace that includes a body, a controller, and a sensor device disposed in the body. The sensor device can include a sensor that is configured to measure at least one parameter associated with a position of the housing. The controller can be communicably coupled to the sensor device and configured to receive a plurality of measurements of the at least one parameter taken by the sensor device. The controller can also be configured to evaluate each measurement of the plurality of measurements.

In another aspect, the disclosure relates to a sensor device that includes a sensor configured to measure at least one parameter associated with a position of a brace in which the sensor is configured to be disposed. The sensor device can also include a controller communicably coupled to the sensor. The controller can be configured to receive a plurality of measurements of the at least one parameter taken by the sensor. The controller can also be configured to evaluate each measurement of the plurality of measurements against at least one threshold value. The controller can further be configured to determine, based on evaluating each measurement, an amount of movement of the brace.

These and other aspects, objects, features, and embodiments will be apparent from the following description and the appended claims.

BRIEF DESCRIPTION OF THE DRAWINGS

The drawings illustrate only example embodiments and are therefore not to be considered limiting in scope, as the example embodiments may admit to other equally effective embodiments. The elements and features shown in the drawings are not necessarily to scale, emphasis instead being placed upon clearly illustrating the principles of the example embodiments. Additionally, certain dimensions or positions may be exaggerated to help visually convey such principles. In the drawings, reference numerals designate like or corresponding, but not necessarily identical, elements.

DETAILED DESCRIPTION

Figure 1:
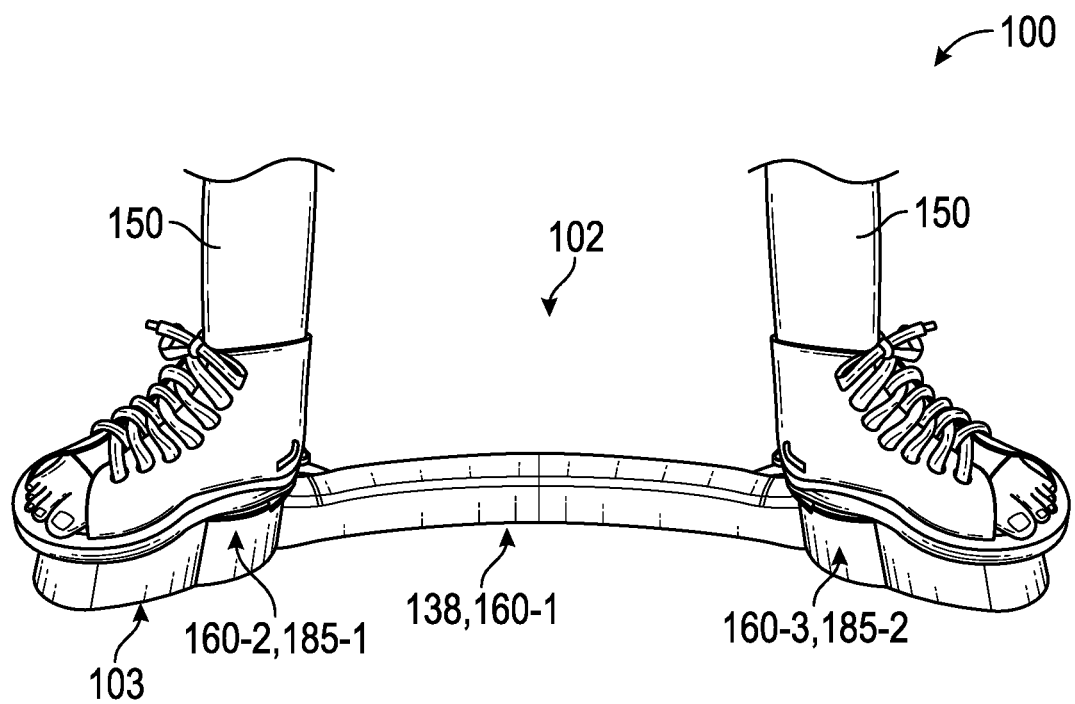
FIGS. 1 through 3 each shows a foot abduction brace that includes a sensor according to certain example embodiments.

In general, example embodiments provide systems, methods, and devices for using sensors to detect movement and/or use of braces used for foot abduction to treat conditions such as clubfoot. Example embodiments for using sensors to detect movement and/or use of braces provide a number of benefits. Such benefits can include, but are not limited to, increased utilization of a brace and improved treatment of a person using the brace. Example embodiments can be used with new braces or retrofit with existing braces.

While examples embodiments are directed to foot abduction braces used to treat clubfoot, example embodiments can be used with braces that can be used to treat any of a number of other conditions that can be used to treat any other part of the body (e.g., a leg, an arm, a wrist). The conditions treated using a brace with example embodiments can be chronic or temporary. Braces that include example embodiments can be used in one or more of any of a number of environments. Examples of such environments can include, but are not limited to, indoors, outdoors, in wet environments, in humid environments, in high-impact environments (e.g., when the brace is used on a ceramic tile or hardwood floor), high vibration environments (e.g., as a result of frequent contact with a hard surface), a dusty or dirty environment, in high temperature environments, in low temperature environments, and in dry environments. Braces that include example embodiments can be subject to stationary conditions, casual use, or active use.

The example braces that include example embodiments can be made of one or more of a number of suitable materials to allow the brace and/or other associated components of a system to meet certain standards and/or regulations while also maintaining durability in light of the one or more conditions under which the brace and/or other associated components of the brace can be exposed. Examples of such materials can include, but are not limited to, aluminum, stainless steel, fiberglass, glass, plastic, ceramic, and rubber.

Example braces (or portions thereof) that include example embodiments described herein can be made from a single piece (as from a mold, injection mold, die cast, or extrusion process). In addition, or in the alternative, braces (or portions thereof) that include example embodiments can be made from multiple pieces that are mechanically coupled to each other. In such a case, the multiple pieces can be mechanically coupled to each other using one or more of a number of coupling methods, including but not limited to epoxy, welding, fastening devices, compression fittings, mating threads, snap fittings, and slotted fittings. One or more pieces that are mechanically coupled to each other can be coupled to each other in one or more of a number of ways, including but not limited to fixedly, hingedly, removeably, slidably, and threadably.

In the foregoing figures showing example embodiments of using sensors to detect movement and/or use of braces, one or more of the components shown may be omitted, repeated, and/or substituted. Accordingly, example embodiments of using sensors to detect movement and/or use of braces should not be considered limited to the specific arrangements of components shown in any of the figures. For example, features shown in one or more figures or described with respect to one embodiment can be applied to another embodiment associated with a different figure or description.

In certain example embodiments, braces that include example embodiments are subject to meeting certain standards and/or requirements. Examples of entities that create, maintain, and/or enforce such standards and requirements can include, but are not limited to, Underwriters Laboratories (UL), the Consumer Product Safety Commission, and the European Commission. Use of example embodiments described herein meet (and/or allow a corresponding brace to meet) such standards when applicable. Examples of such standards can include, but are not limited to, EN60950, UL2300, and electromagnetic compatibility (EMC) standards.

If a component of a figure is described but not expressly shown or labeled in that figure, the label used for a corresponding component in another figure can be inferred to that component. Conversely, if a component in a figure is labeled but not described, the description for such component can be substantially the same as the description for the corresponding component in another figure. The numbering scheme for the various components in the figures herein is such that each component is a three-digit number, and corresponding components in other figures have the identical last two digits.

In addition, a statement that a particular embodiment (e.g., as shown in a figure herein) does not have a particular feature or component does not mean, unless expressly stated, that such embodiment is not capable of having such feature or component. For example, for purposes of present or future claims herein, a feature or component that is described as not being included in an example embodiment shown in one or more particular drawings is capable of being included in one or more claims that correspond to such one or more particular drawings herein.

Example embodiments of using sensors to detect movement and/or use of braces will be described more fully hereinafter with reference to the accompanying drawings, in which example embodiments of using sensors to detect movement and/or use of braces are shown. Using sensors to detect movement and/or use of braces may, however, be embodied in many different forms and should not be construed as limited to the example embodiments set forth herein. Rather, these example embodiments are provided so that this disclosure will be thorough and complete, and will fully convey the scope of using sensors to detect movement and/or use of braces to those of ordinary skill in the art. Like, but not necessarily the same, elements (also sometimes called components) in the various figures are denoted by like reference numerals for consistency.

Terms such as "first", "second", "above", "below", "distal", "proximal", "end", "top", "bottom", "side", and "within" are used merely to distinguish one component (or part of a component or state of a component) from another. Such terms are not meant to denote a preference or a particular orientation. Such terms are not meant to limit embodiments of using sensors to detect movement and/or use of braces. In the following detailed description of the example embodiments, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Figure 2:
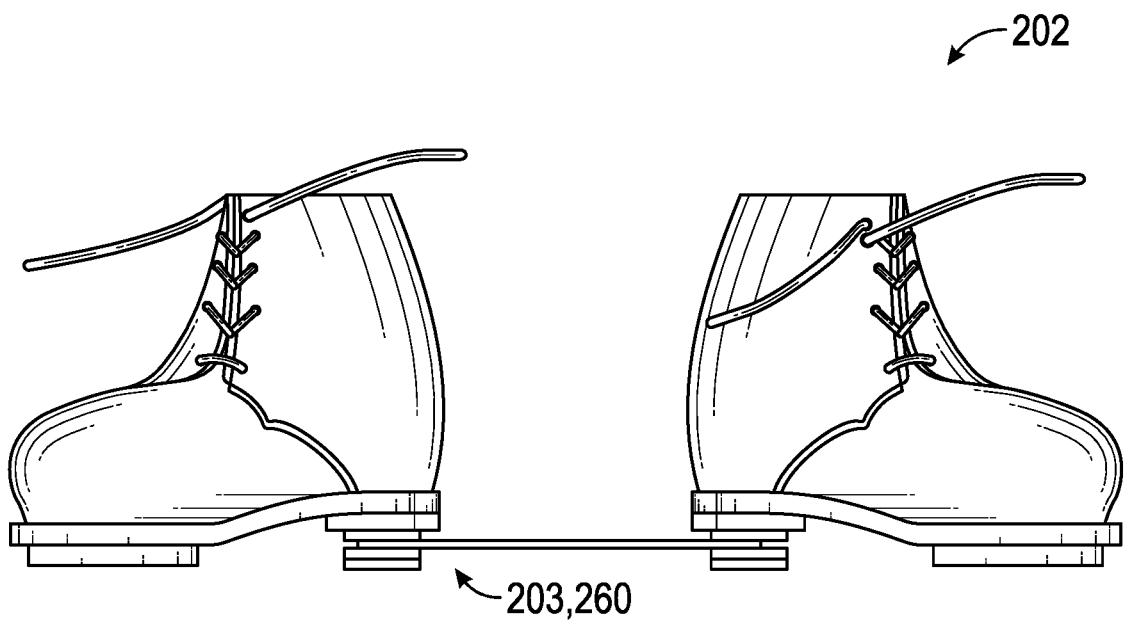
Figure 3:
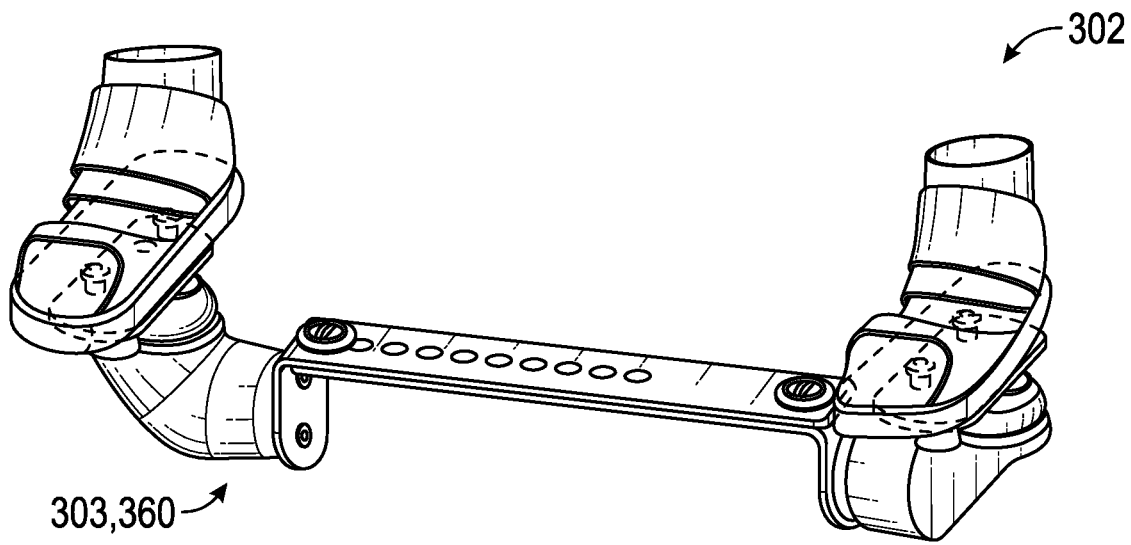

FIGS. 1 through 3 show various braces that can include sensor devices according to certain example embodiments. Specifically, FIG. 1 shows a system 100 that includes a brace 102 worn by a user 150. FIG. 2 shows another brace 202. FIG. 3 shows yet another brace 302. The brace 102 of FIG. 1, the brace 202 of FIG. 2, and the brace 302 of FIG. 3 can be used to treat clubfoot.

The brace 102 of FIG. 1 includes a body 103, which has three sensor devices 160 (sensor device 160-1, sensor device 160-2, and sensor device 160-3) disposed therein. The sensor device 160-1 is integrated with a central portion 138 (also called a base 138 or a crossbar 138) of the body 103. In addition, the sensor device 160-2 is disposed within a removable component 185-1 at one end of the body 103 of the brace 102, and the sensor device 160-3 is disposed within a removable component 185-2 at the opposite end of the body 103 of the brace 102. More details about braces with removable components hosting sensor devices are discussed below with respect to FIGS. 8A through 9E. The brace 202 of FIG. 2 includes a body 203, which has a sensor device 260 disposed therein. The brace 302 of FIG. 3 includes a body 303, which has a sensor device 360 disposed therein.

Figure 4:
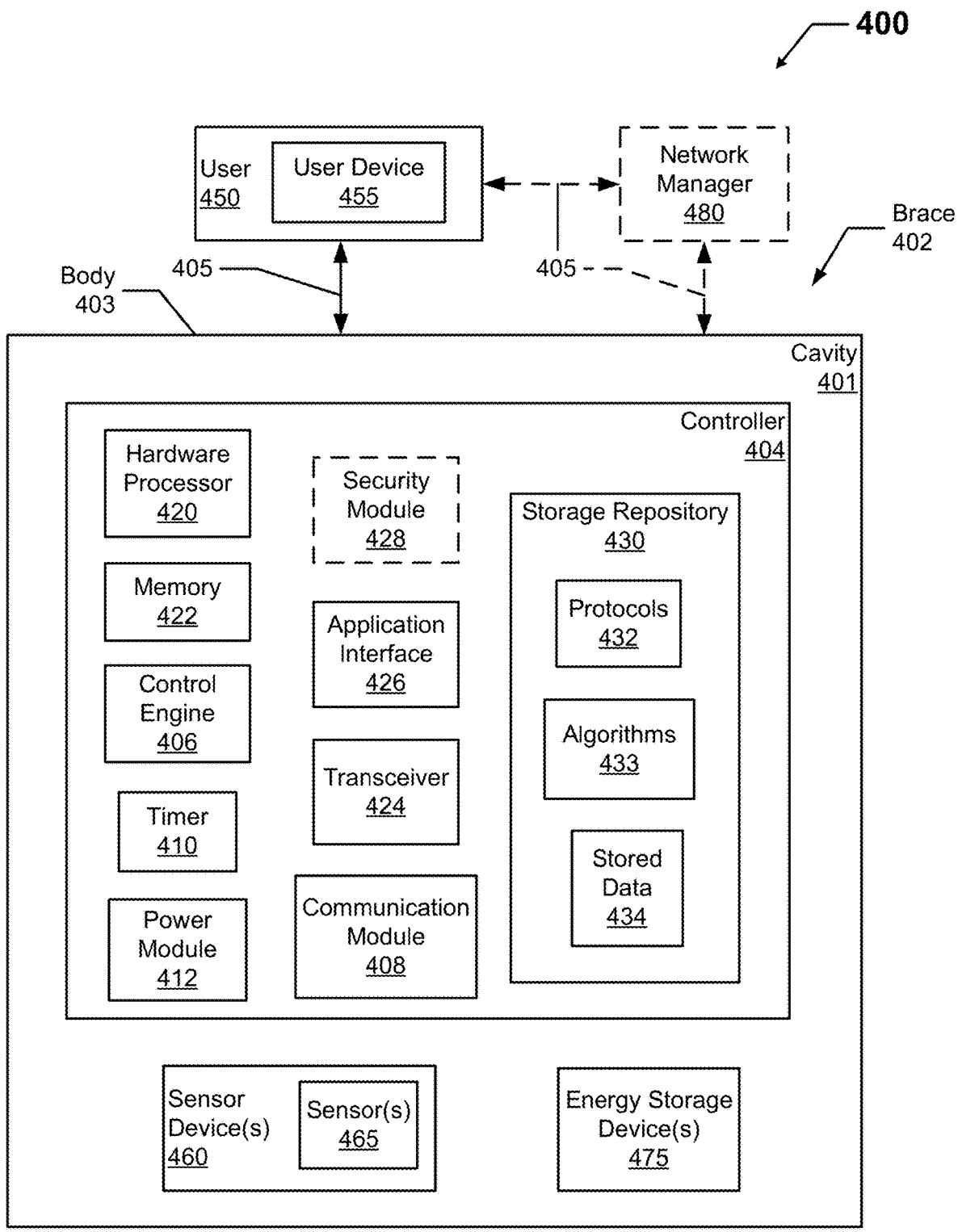
FIG. 4 shows a system diagram of a system that includes a brace with a sensor according to certain example embodiments.

FIG. 4 shows a system diagram of a system 400 that includes a brace 402 having one or more example sensor devices 460 according to certain example embodiments. In this case, since the brace 402 has a controller 404, the one or more example sensor devices 460 rely upon a number of capabilities of the controller 404 to help the controller 404 determine whether the brace 402 has experienced significant movement and/or other indications of use.

The system 400 can include one or more users 450 (where each user can include one or more user devices 455), an optional network manager 480, and the brace 402. In addition to the controller 404, the brace 402 can include the one or more sensor devices 460 and one or more energy storage devices 475. The controller 404 can include one or more of a number of components. Such components, can include, but are not limited to, a control engine 406, a communication module 408, a timer 410, a power module 412, a storage repository 430, a hardware processor 420, a memory 422, a transceiver 424, an application interface 426, and, optionally, a security module 428. The components shown in FIG. 4 are not exhaustive, and in some embodiments, one or more of the components shown in FIG. 4 may not be included in an example braces 402. Any component of the example brace 402 can be discrete or combined with one or more other components of the brace 402.

Referring to FIGS. 1 through 4, a user 450 may be any person that interacts with the brace 402. Examples of a user 450 may include, but are not limited to, a child with clubfoot, a doctor, a nurse, an engineer, a technician, a consultant, a contractor, and a manufacturer's representative. A user 450 can use a user device 455, which may include a display (e.g., a GUI). A user 450 (including an associated user device 455) can interact with (e.g., sends data to, receives data from) the controller 404 of the brace 402 via the application interface 426 (described below). A user 450 (including an associated user device 455) can also interact with the network manager 480.

Interaction between a user 450 (including an associated user device 455), the brace 402, and the network manager 480 can be conducted using communication links 405. Each communication link 405 can include wired (e.g., Class 1 electrical cables, Class 2 electrical cables, electrical connectors) and/or wireless (e.g., Wi-Fi, Zigbee, visible light communication, cellular networking, Bluetooth, WirelessHART, ISA100, Power Line Carrier, RS485) technology. The communication link 405 can transmit signals (e.g., power signals, communication signals, control signals, data) between the brace 402, a user 450 (including an associated user device 455), and the optional network manager 480.

The optional network manager 480 is a device or component that controls all or a portion of system 400 that includes the controller 404 of the brace 402 and a user 450 (including an associated user device 455) in the system 400. The network manager 480 can be substantially similar to the controller 404. Alternatively, the network manager 480 can include one or more of a number of features and/or components in addition to, or altered from, the features and/or components of the controller 404 described below. As described herein, communication with the network manager 480 can include communicating with one or more other components of the system 400. In such a case, the network manager 480 can facilitate such communication.

A user 450 (including an associated user device 455) and the network manager 480 can interact with the controller 404 of the brace 402 using the application interface 426 according to one or more example embodiments. Specifically, the application interface 426 of the controller 404 receives data (e.g., information, communications, instructions, updates to firmware) from and sends data (e.g., information, communications, instructions) to a user 450 (including an associated user device 455) and the network manager 480. A user 450 (including an associated user device 455) and the network manager 480 can include an interface to receive data from and send data to the controller 404 of the brace 402 in certain example embodiments. Examples of such an interface can include, but are not limited to, a graphical user interface, a touchscreen, an application programming interface, a keyboard, a monitor, a mouse, a web service, a data protocol adapter, some other hardware and/or software, or any suitable combination thereof.

The controller 404, each user 450 (including an associated user device 455), and the network manager 480 can use their own system or share a system in certain example embodiments. Such a system can be, or contain a form of, an Internet-based or an intranet-based computer system that is capable of communicating with various software. A computer system includes any type of computing device and/or communication device, including but not limited to the controller 404. Examples of such a system can include, but are not limited to, a desktop computer with Local Area Network (LAN), Wide Area Network (WAN), Internet or intranet access, a laptop computer with LAN, WAN, Internet or intranet access, a smart phone, a server, a server farm, an android device (or equivalent), a tablet, smartphones, and a personal digital assistant (PDA). Such a system can correspond to a computer system as described below with regard to FIG. 5.

Further, as discussed above, such a system can have corresponding software (e.g., user software, controller software, network manager software). The software can execute on the same or a separate device (e.g., a server, mainframe, desktop personal computer (PC), laptop, PDA, television, cable box, satellite box, kiosk, telephone, mobile phone, or other computing devices) and can be coupled by the communication network (e.g., Internet, Intranet, Extranet, LAN, WAN, or other network communication methods) and/or communication channels, with wire and/or wireless segments according to some example embodiments. The software of one system can be a part of, or operate separately but in conjunction with, the software of another system within the system 400.

The brace 402 can include a body 403. The body 403 (or a portion thereof) can include at least one wall that forms a cavity 401. In some cases, the body 403 can be designed to comply with any applicable standards so that the brace 402 can be located in a particular environment (e.g., outdoors). The body 403 of the brace 402 can include one or more components that are detachably coupled to each other. For example, as shown in FIG. 1, the body 403 of the brace 402 can include a crossbar 138 and two foot restraints that are detachably coupled to the crossbar 138.

The body 403 of the brace 402 can be used to house one or more components of the brace 402, including one or more components of the controller 404. For example, the controller 404 (which in this case includes the control engine 406, the communication module 408, the timer 410, the power module 412, the storage repository 430, the hardware processor 420, the memory 422, the transceiver 424, the application interface 426, and the optional security module 428) and the one or more sensor devices 460 can be disposed in a cavity 401 formed by the body 403. In alternative embodiments, any one or more of these or other components (e.g., a sensor device 460, the controller 404 or portions thereof) of the brace 402 can be disposed on the body 403 and/or remotely from the body 403.

The storage repository 430 can be a persistent storage device (or set of devices) that stores software and data used to assist the controller 404 in communicating with a user 450 (including an associated user device 455) and the network manager 480 within the system 400. The software and data stored in the storage repository 430 can also be used to help the controller 404 carry out its various functions, including determining, based on measurements made by one or more of the sensor devices 460, whether the brace 402 (or portion thereof) has been significantly moved from a previous position. In one or more example embodiments, the storage repository 430 stores one or more protocols 432, one or more algorithms 433, and stored data 434.

The protocols 432 can include any processes or logic steps that are implemented by the control engine 406 based on certain conditions at a point in time. The protocols 432 can include communication protocols that are used to send and/or receive data between the controller 404, a user 450 (including an associated user device 455), and the network manager 480. One or more of the protocols 432 can be a time-synchronized protocol for communications. Examples of such time-synchronized protocols can include, but are not limited to, a highway addressable remote transducer (HART) protocol, a wirelessHART protocol, and an International Society of Automation (ISA) 100 protocol. In this way, one or more of the protocols 432 can provide a layer of security to the data transferred within the system 400.

An example of a protocol 432 is measuring, using a sensor device 460, an amount of movement and/or a change in orientation of the body 403 and/or some other portion of the brace 402. Another example of a protocol 432 is to send a communication when an amount of movement and/or change in orientation of the brace 402 (or portion thereof) exceeds a threshold value. A protocol 432 can then be used to determine whether the control engine 406 should generate a notification (e.g., to a user 450 (including an associated user device 455), to the network manager 480) regarding movement of the brace 402.

The algorithms 433 can be any models, formulas, and/or other similar operational implementations that the control engine 406 of the controller 404 uses. An example of an algorithm 4332 is using measurements made by a sensor module 460 to determine (e.g., calculate) an amount of movement and/or a change in orientation of the brace 402. For instance, an algorithm 433 can include a formula or model that compares measurements (or results of calculations made using those measurements) made by one or more of the sensor devices 460 with threshold values (part of the stored data 434). One or more algorithms 433 can at times be used in conjunction with one or more protocols 432.

Stored data 434 can be any historical, present, and/or forecast data. Stored data 134 can be associated with a sensor device 460, the controller 404, the network manager 480, and a user 450 (including an associated user device 455). Stored data can be associated with the brace 402 or portion thereof. Such stored data 434 can include, but is not limited to, settings, threshold values, default values, user preferences, results of an algorithm 433, a manufacturer of a sensor device 460, a model number of a sensor device 460, and measurements taken by the sensor device 460.

Examples of a storage repository 430 can include, but are not limited to, a database (or a number of databases), a file system, a hard drive, flash memory, cloud-based storage, some form of solid-state data storage, or any suitable combination thereof. The storage repository 430 can be located on multiple physical machines, each storing all or a portion of the protocols 432, the algorithms 433, and/or the stored data 434 according to some example embodiments. Each storage unit or device of the storage repository 430 can be physically located in the same or in a different geographic location.

The storage repository 430 can be operatively connected to the control engine 406. In one or more example embodiments, the control engine 406 includes functionality to communicate with a user 450 (including an associated user device 455) and the network manager 480. More specifically, the control engine 406 sends information to and/or receives information from the storage repository 430 in order to communicate with a user 450 (including an associated user device 455) and the network manager 480. As discussed below, the storage repository 430 can also be operatively connected to the communication module 408 in certain example embodiments.

In certain example embodiments, the control engine 406 of the controller 404 controls the operation of one or more components (e.g., the communication module 408, the timer 410, the transceiver 424) of the controller 404. For example, the control engine 406 can activate the communication module 408 when the communication module 408 is in "sleep" mode and when the communication module 408 is needed to send data received from another component (e.g., a sensor device 460, a user device 455) in the system 400. As another example, the control engine 406 can operate one or more sensor devices 460 to dictate when measurements are taken by the sensor devices 460 and when those measurements are communicated by the sensor devices 460 to the control engine 406. As another example, the control engine 406 can acquire the current time using the timer 410. The timer 410 can enable the controller 404 even when the controller 404 has no communication with the network manager 480.

As another example, the control engine 406 can store configurations of the controller 404 (or portions thereof) in memory 422 (e.g., non-volatile memory) so that the controller 404 (or portions thereof) can operate regardless of whether the controller 404 is communicating with the network manager 480 and/or other components in the system 400. As still another example, the control engine 406 can conduct one or more tests, according to a protocol 432 and/or an algorithm 433, to determine whether movement of the brace 402 has exceeded one or more threshold values based on measurements made by one or more sensor devices 460.

In certain example embodiments, the control engine 406 can identify and report the type of movement of the brace 402 using one or more protocols 432 and/or algorithms 433, which can be based on one or more threshold values against which measurements made by a sensor device 460 can be compared. For example, the control engine 406 can determine whether a measurement or series of measurements made by a sensor device 460 indicates the brace 402 is being used to walk, that the brace 402 is being worn, or that the brace 402 is being moved without being worn. Such threshold values can be, for example, a plus-or-minus degree of movement, an amount of time that a degree of movement has been sustained, an amount of pressure or a weight measured by a sensor device 460, a temperature measured by a sensor device 460, and an amount of movement relative to a default position in a period of time.

The control engine 406 can follow a protocol 432 to control (e.g., when measurements should be taken, how often measurements should be taken, which measurements should be taken) each sensor device 460. As yet another example, the control engine 406 can determine when to communicate with a user 450 (including an associated user device 455) and/or the network manager 480 based on whether the control engine 406 has determined, using protocols 432 and/or algorithms 433 in combination with measurements made by one or more sensor devices 460, that the brace 402 has moved a significant amount. As still another example, the control engine 406 can cause the controller 404 to operate in an autonomous control mode if one or more components (e.g., the communication module 408, the transceiver 424) of the controller 404 that allows the controller 404 to communicate with another component of the system 400 fails.

The control engine 406 can provide control, communication, and/or other similar signals to a user 450 (including an associated user device 455) and the network manager 480. Similarly, the control engine 406 can receive control, communication, and/or other similar signals from a user 450 (including an associated user device 455) and the network manager 480. The control engine 406 can control each sensor device 460 automatically (for example, based on one or more protocols 432 and/or algorithms 433 stored in the storage repository 430) and/or based on control, communication, and/or other similar signals received from another component (e.g., the network manager 480, a user device 455) through a communication link 405. The control engine 406 may include a printed circuit board, upon which the hardware processor 420 and/or one or more discrete components of the controller 404 are positioned.

In certain example embodiments, the control engine 406 can include an interface that enables the control engine 406 to communicate with one or more components (e.g., a sensor device 455) of the brace 402. The controller 404 can include an interface that can operate in conjunction with, or independently of, the protocols 432 used to communicate between the controller 404, a user 450 (including an associated user device 455) and the network manager 480. The interface can allow for addressable communications between the controller 404, the user 450 (including an associated user device 455), and the network manager 480.

The control engine 406 (or other components of the controller 404) can also include one or more hardware components and/or software elements to perform its functions. Such components can include, but are not limited to, a universal asynchronous receiver/transmitter (UART), a serial peripheral interface (SPI), a direct-attached storage (DAS) device, an analog-to-digital converter, an inter-integrated circuit ($I^2C$), and a pulse width modulator (PWM).

The communication module 408 of the controller 404 determines and implements the communication protocol (e.g., from the protocols 432 of the storage repository 430) that is used when the control engine 406 communicates with (e.g., sends signals to, receives signals from) a user 450 (including an associated user device 455), the network manager 480, and/or one or more of the sensor devices 460. In some cases, the communication module 408 accesses the stored data 434 to determine which protocol 432 is used to communicate with the sensor device 460 associated with the stored data 434. In addition, the communication module 408 can interpret the protocol 432 of a communication received by the controller 404 so that the control engine 406 can interpret the communication.

The communication module 408 can send and receive data between the network manager 480, the users 450 (including associated user devices 455), the sensor devices 455, and the controller 404. The communication module 408 can send and/or receive data in a given format that follows a particular protocol 432 for communication. The control engine 406 can interpret the data packet received from the communication module 408 using information about a protocol 432 stored in the storage repository 430. The control engine 406 can also facilitate the data transfer between the network manager 480, the sensor devices 455, and/or a user 450 (including an associated user device 455) by converting the data into a format understood by the communication module 408.

The communication module 408 can send data (e.g., protocols 432, algorithms 433, stored data 434, measurements made by a sensor device 460, operational information, error codes, threshold values, user preferences) directly to and/or retrieve data directly from the storage repository 430. Alternatively, the control engine 406 can facilitate the transfer of data between the communication module 408 and the storage repository 430. The communication module 408 can also provide encryption to data that is sent by the controller 404 and decryption to data that is received by the controller 404. The communication module 408 can also provide one or more of a number of other services with respect to data sent from and received by the controller 404. Such services can include, but are not limited to, data packet routing information and procedures to follow in the event of data interruption.

The timer 410 of the controller 404 can track clock time, intervals of time, an amount of time, and/or any other measure of time. The timer 410 can also count the number of occurrences of an event, whether with or without respect to time. Alternatively, the control engine 406 can perform the counting function. The timer 410 is able to track multiple time measurements concurrently. The timer 410 can track time periods based on an instruction received from the control engine 406, based on an instruction received from a user 450 (including an associated user device 455), based on an instruction programmed in the software for the controller 404, based on some other condition or from some other component, or from any combination thereof.

The timer 410 can be configured to track time when there is no power delivered to the controller 404 (e.g., the power module 412 malfunctions) using, for example, a super capacitor or a battery backup. In such a case, when there is a resumption of power delivery to the controller 404, the timer 410 can communicate any aspect of time to the controller 404. In such a case, the timer 410 can include one or more of a number of components (e.g., a super capacitor, an integrated circuit) to perform these functions.

The power module 412 of the controller 404 provides power to one or more other components (e.g., timer 410, control engine 406) of the controller 404. In addition, in certain example embodiments, the power module 412 can provide power to one or more sensor modules 460 of the brace 402. The power module 412 can include one or more of a number of single or multiple discrete components (e.g., transistor, diode, resistor), and/or a microprocessor. The power module 412 may include a printed circuit board, upon which the microprocessor and/or one or more discrete components are positioned. In some cases, the power module 412 can include one or more components that allow the power module 412 to measure one or more elements of power (e.g., voltage, current) that is delivered to and/or sent from the power module 412.

The power module 412 can include one or more components (e.g., a transformer, a diode bridge, an inverter, a converter) that receives power (for example, through an electrical cable) from one or more energy storage devices 475 and/or a source external to the brace 402. The power module 412 can use this power to generate power of a type (e.g., alternating current, direct current) and level (e.g., 12V, 24V, 120V) that can be used by the other components of the controller 404. In addition, or in the alternative, the power module 412 can be or include a source of power in itself to provide signals to the other components of the controller 404 and/or the power supply 440. For example, the power module 412 can include a battery or other form of energy storage device, such as energy storage device 475. As another example, the power module 412 can include a localized photovoltaic solar power system.

As discussed above, in certain example embodiments, the power module 412 of the controller 404 can also provide power and/or control signals, directly or indirectly, to one or more of the sensor devices 460. In such a case, the control engine 406 can direct the power generated by the power module 412 to the sensor devices 460 of the brace 402. In this way, power can be conserved by sending power to the sensor devices 460 of the brace 402 when those devices need power, as determined by the control engine 406.

The hardware processor 420 of the controller 404 executes software, algorithms (e.g., algorithms 433), and firmware according to one or more example embodiments. Specifically, the hardware processor 420 can execute software on the control engine 406 or any other portion of the controller 404, as well as software used by a user 450, any other brace 402-N, and/or the network manager 480. The hardware processor 420 can be or include an integrated circuit (IC), a central processing unit, a multi-core processing chip, SoC, a multi-chip module including multiple multi-core processing chips, or other hardware processor in one or more example embodiments. The hardware processor 420 can be known by other names, including but not limited to a computer processor, a microprocessor, and a multi-core processor.

In one or more example embodiments, the hardware processor 420 executes software instructions stored in memory 422. The memory 422 includes one or more cache memories, main memory, and/or any other suitable type of memory. The memory 422 can include volatile and/or non-volatile memory. The memory 422 is discretely located within the controller 404 relative to the hardware processor 420 according to some example embodiments. In certain configurations, the memory 422 can be integrated with the hardware processor 420.

In certain example embodiments, the controller 404 does not include a hardware processor 420. In such a case, the controller 404 can include, as an example, one or more field programmable gate arrays (FPGA), one or more insulated-gate bipolar transistors (IGBTs), and/or one or more ICs. Using FPGAs, IGBTs, ICs, and/or other similar devices known in the art allows the controller 404 (or portions thereof) to be programmable and function according to certain logic rules and thresholds without the use of a hardware processor. Alternatively, FPGAs, IGBTs, ICs, and/or similar devices can be used in conjunction with one or more hardware processors 420.

The transceiver 424 of the controller 404 can send and/or receive control and/or communication signals. Specifically, the transceiver 424 can be used to transfer data between the controller 404, a user 450, any other brace 402-N, and the network manager 480. The transceiver 424 can use wired and/or wireless technology. The transceiver 424 can be configured in such a way that the control and/or communication signals sent and/or received by the transceiver 424 can be received and/or sent by another transceiver that is part of a user 450, any other brace 402-N, and/or the network manager 480. The transceiver 424 can use any of a number of signal types, including but not limited to radio frequency signals and visible light signals.

When the transceiver 424 uses wireless technology, any type of wireless technology and/or protocol can be used by the transceiver 424 in sending and receiving signals. Such wireless technologies and/or protocols can include, but are not limited to, Wi-Fi, Zigbee, visible light communication, cellular networking, Bluetooth, and Bluetooth Low Energy. The transceiver 424 can use one or more of any number of suitable protocols 432 (e.g., ISA100, HART) when sending and/or receiving signals. Such communication protocols can be stored in the protocols 432 of the storage repository 430. Further, any transceiver information for a user 450, any other brace 402-N, and the network manager 480 can be part of the protocols 432 (or other areas) of the storage repository 430.

Optionally, in one or more example embodiments, the security module 428 secures interactions between the controller 404, the users 450, any other brace 402-N, and the network manager 480. More specifically, the security module 428 authenticates communication from software based on security keys verifying the identity of the source of the communication. For example, user software may be associated with a security key enabling the software of a user 450 to interact with the controller 404. Further, the security module 428 can restrict receipt of information, requests for information, and/or access to information in some example embodiments.

As mentioned above, aside from the controller 404 and its components, the brace 402 can include one or more sensor devices 460. A sensor device 460 can include one or more sensors 465. The sensor 465 of each sensor device 460 measures one or more parameters (e.g., position, azimuth, direction, acceleration, vibration, oscillation, pressure, temperature, carbon dioxide, humidity, weight). The sensor 465 of each sensor device 460 can be any type of sensor 465 that measures one or more parameters. Examples of types of sensors 465 of sensor devices 460 can include, but are not limited to, a mercury switch, an accelerometer, a compass, a vibration sensor, an antenna, a resistor, a humidity sensor, a pressure sensor, an air flow monitor, a gas detector, a load cell, and a resistance temperature detector. The brace 402 can include one or more sensor devices 460. A sensor device 460 can have one or multiple sensors 465.

In example embodiments, one or more of the sensor devices 460 are used to measure parameters relating to the position (e.g., in two dimensions, in three dimensions) of the brace 402. For example, a sensor 465 of a sensor device 460 can be used to measure whether the brace 402 (or some component thereof, such as the body 403) is vibrating or oscillating (e.g., as when someone (e.g., a user 450) is wearing the brace 402) or is put in a new position (e.g., in two dimensions, in three dimensions).

In addition to a sensor 465, a sensor device 460 can include one or more other components. For instance, an example of an integrated sensor device 560 is shown below with respect to FIG. 5. As another example, a sensor 465 of a sensor device 460 of the brace 402 can include an antenna for sending and/or receiving signals (e.g., with a user device 455, with the network manager 480). Such signals can include instructions for operating the sensor device 460 and measurements made by the sensor 465 of the sensor device 460. In some cases, the signals received by a sensor device 460 and/or sent by a sensor device 460 can include a UUID of the sending component of the system 400 and/or the sensor device, respectively.

In some cases, a number of sensors 465 and/or sensor devices 460, each measuring a different parameter, can be used in combination to determine and confirm whether the brace 402 is being worn by a user 450, for how long, and/or in what fashion. For example, multiple sensors 465 can be used to determine if a user 450 is trying to move (e.g., walk)

while wearing the brace 402. For example, one sensor 465 of the brace 402 can include a gyroscope that determines movement (e.g., in two dimensions, in three dimensions) of the brace 402, while another sensor 465 of the brace 402 can include a pressure sensor that measures an amount of pressure applied to a footplate of the brace 402. In such a case, the gyroscope indicates a significant movement of the brace 402, and a threshold amount of pressure detected by the other sensor 465 indicates that a user 450 is walking while wearing the brace 402. Each sensor device 460 can use one or more of a number of protocols 432 for operations and/or communication.

A sensor 465 of a sensor device 460 can be disposed at any location on or within the body 403 of the brace 402. For example, a sensor 465 of a sensor device 460 can be disposed within a foot restraint (part of the body 403) of the brace 402. As another example, a sensor 465 of a sensor device 460 can be disposed within a base (part of the body 403) of the brace 402. As a specific example, FIG. 1 shows that the brace 102 has a sensor device 160-2 disposed in a removable portion 185-1 on one side of the body 103, a second sensor device 160-3 disposed in a removable portion 185-2 on the opposite side of the body 403, and a third sensor device 160-1 disposed in the crossbar 138 of the body 403.

Each of the one or more energy storage devices 475 can include one or more batteries, supercapacitors, and/or other components that can store and subsequently release power. The power provided by the energy storage device 475 can be of a type (e.g., direct current, alternating current) and of a level (e.g., 12V, 24V) that are used by the recipient component (e.g., a sensor device 460, the controller 404) of the brace 402. There can be any number of energy storage devices 475. When an energy storage device 475 includes battery units, the battery units can use one or more of any number of battery technologies. Examples of such technologies can include, but are not limited to, nickel-cadmium, nickel-metalhydride, lithium-ion, and alkaline. In certain example embodiments, one or more of the battery units can be rechargeable.

As stated above, the brace 402 can be placed in any of a number of environments. As a result, the body 403 of the brace 402 can be configured to comply with applicable standards for any of a number of environments. For example, the brace 402 can be rated as a Division 1 or a Division 2 enclosure under NEC standards. Similarly, any of the sensor devices 460 or other devices communicably coupled to the brace 402 can be configured to comply with applicable standards for any of a number of environments. For example, the body 403 can be rated as a Division 1 or a Division 2 enclosure under NEC standards.

An example sensor device 460 described herein can be a permanent part of the brace 402. In other words, the sensor device 460 can be hardwired, embedded within, and/or otherwise fixedly attached to some part (e.g., the housing 403) of the brace 402. In other cases, an example sensor device 460 can be removably coupled to and/or retrofittable with respect to the brace 402. For example, a sensor device 460 can be integrated with the rest of the brace 402 during manufacturing, during installation, or after installation and operation. As another example, the location of a sensor device 460 with respect to the body 403 of the brace 402 can vary. In addition, in some cases, a sensor device 460 is configured to have coupling features (e.g., plugs, clamps) that allow the sensor device 460 to be easily replaced by a user 450 after installation if that sensor device 460 fails, malfunctions, or does not have the desired type of sensing device 465.

In some cases, the body 403 of the brace 402 can have an access panel or some other similar feature that allows a user 450 to access a sensor device 460, the controller 404, and/or some other component (e.g., a battery or other type of energy storage device 475) of the brace 402. In such a case, the access panel can be configured to be tamper proof or can only be accessed using a tool (e.g., a screwdriver, a wrench) so that children are unable to access the components behind the panel, thereby ensuring reliable operation of the sensor device 460 and controller 406 while also avoiding a choking hazard that these components can present to a child. An example of this can be found in FIGS. 8A through 9E below.

Figure 5:
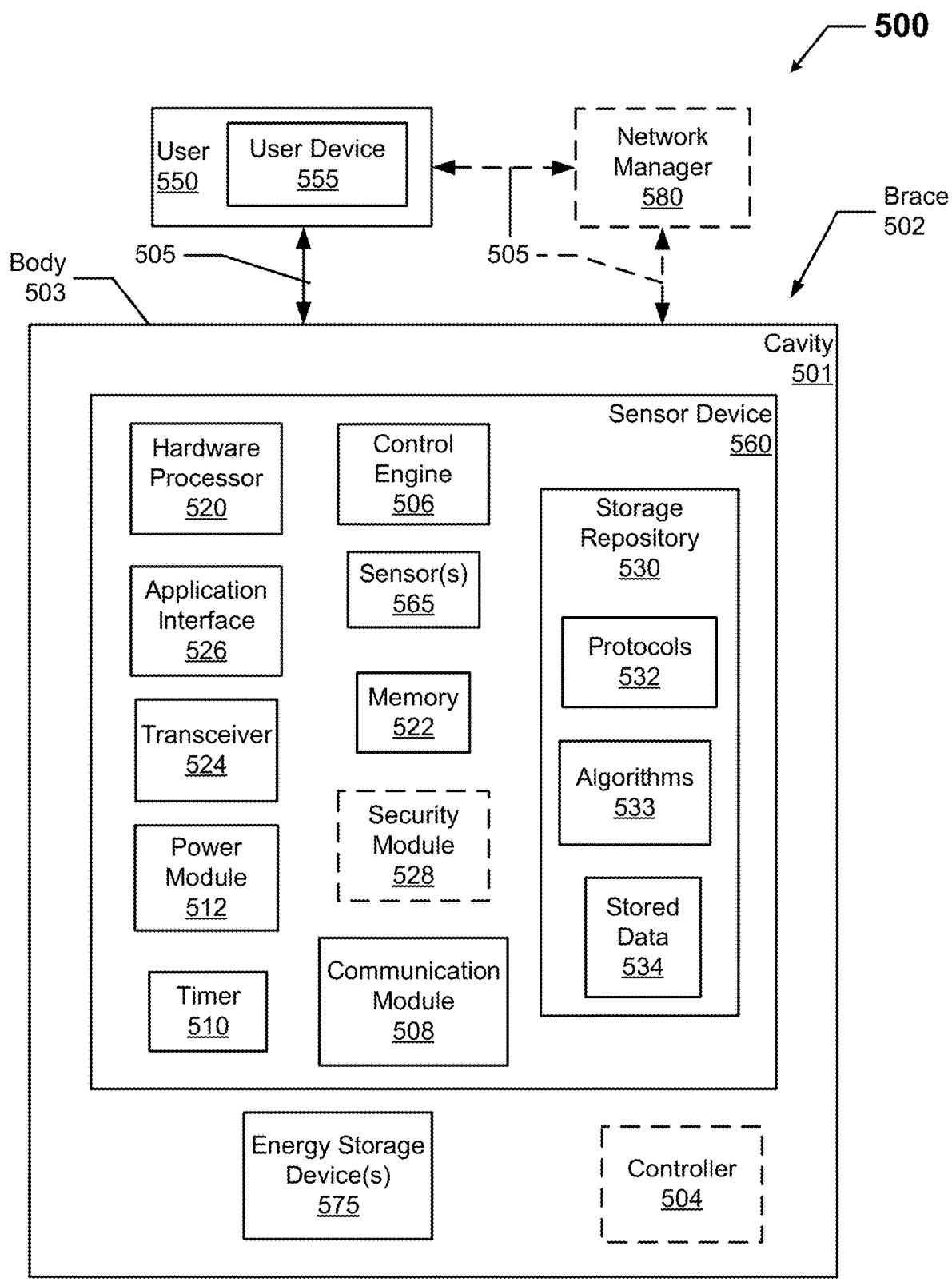
FIG. 5 shows a system diagram of another system that includes a brace with a sensor according to certain example embodiments.

FIG. 5 shows a system diagram of another system 500 that includes a brace 502 having an example integrated sensor device 560 according to certain example embodiments. In this case, the controller 504 of the brace 502 is optional, and so the example integrated sensor device 560 includes a number of capabilities of the controller 404 of FIG. 4 described above to allow the integrated sensor device 560 to autonomously determine whether the brace 502 has experienced significant movement and measure the amount of use that the brace 502 is undergoing by a user 550. The brace 502 also includes one or more energy storage devices 575.

Referring to FIGS. 1 through 5, the system 500 of FIG. 5 can include one or more users 550 (which can each include one or more user devices 555), an optional network manager 580, the brace 502. The sensor device 560 can include one or more of a number of components. Such components, can include, but are not limited to, a sensor 565, a control engine 506, a communication module 508, a timer 510, a power module 512, a storage repository 530, a hardware processor 520, a memory 522, a transceiver 524, an application interface 526, and, optionally, a security module 528. The storage repository 530 can include one or more protocols 532, one or more algorithms 533, and stored data 534. The brace 502 can include a body 503 that forms one or more cavities 501.

The various components (including portions thereof) shown in FIG. 5 can be substantially the same as the corresponding components (including corresponding portions thereof) shown in FIG. 4, except that the control engine 506, the communication module 508, the timer 510, the power module 512, the storage repository 530, the hardware processor 520, the memory 522, the transceiver 524, the application interface 526, and, the optional security module 528 are part of the sensor device 560 rather than the optional controller 504, thereby making the sensor device 560 of FIG. 5 integrated. If the brace 502 does include a controller 504, then the controller 504 can include a control engine, a communication module, a timer, a power module, a storage repository, a hardware processor, a memory, a transceiver, an application interface, an optional security module, and/or any other suitable component. In such a case, the components of the controller 504 can act independently of the corresponding components of the sensor device 560. Alternatively, one or more of the components of the sensor device 560 can be shared with the controller 504. In such a case, such a component can be located in a housing of the sensor device 560, on the housing of the sensor device 560, or outside the housing of the sensor device 560.

The brace 502 can include more than one sensor devices 560. In such a case, each additional sensor device 560 can include one or more of the components of the sensor device 560 shown in FIG. 5. In some cases, the components of one sensor device 560 can act independently of the corresponding components of another sensor device 560. Alternatively, one or more of the components of one sensor device 560 can be shared with another sensor device 560. In other words, if the brace 502 of FIG. 5 includes multiple sensor devices 560, one or more of the additional sensor devices 560 may be integrated. In such a case, the sensor device 560 shown in FIG. 5 can control and/or communicate with that additional non-integrated sensor device 560. The various components of the system 500 of FIG. 5 are not exhaustive, and in some embodiments, one or more of the components shown in FIG. 5 may not be included in an example brace. Any component of the example brace 502 can be discrete or combined with one or more other components of the brace 502.

Figure 6:
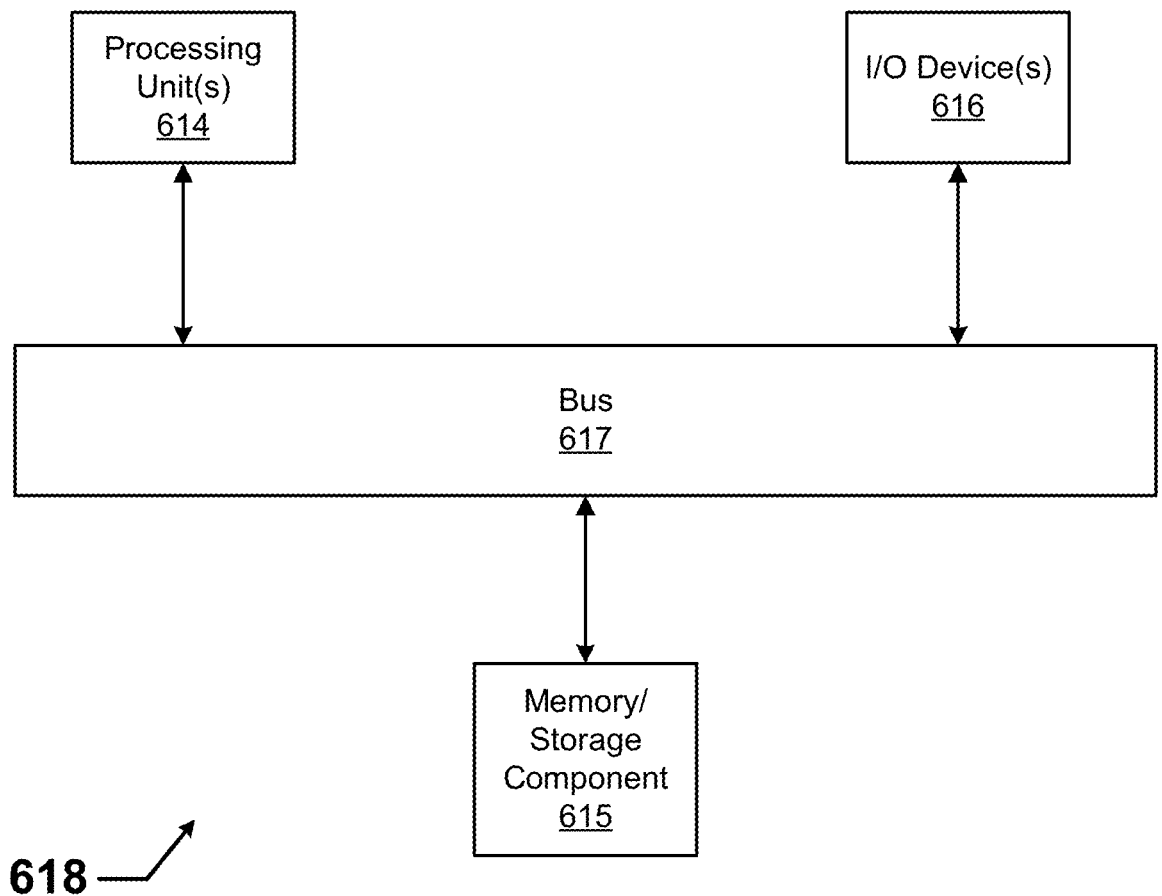
FIG. 6 shows a computing device according to certain example embodiments.

FIG. 6 illustrates one embodiment of a computing device 618 that implements one or more of the various techniques described herein, and which is representative, in whole or in part, of the elements described herein pursuant to certain example embodiments. For example, computing device 618 can be implemented in the brace 402 of FIG. 4 in the form of the hardware processor 420, the memory 422, and the storage repository 430, among other components. As another example, computing device 618 can be implemented in the brace 502 of FIG. 5 in the form of the hardware processor 520, the memory 522, and the storage repository 530, among other components. Computing device 618 is one example of a computing device and is not intended to suggest any limitation as to scope of use or functionality of the computing device and/or its possible architectures. Neither should computing device 618 be interpreted as having any dependency or requirement relating to any one or combination of components illustrated in the example computing device 618.

Computing device 618 includes one or more processors or processing units 614, one or more memory/storage components 615, one or more input/output (I/O) devices 616, and a bus 617 that allows the various components and devices to communicate with one another. Bus 617 represents one or more of any of several types of bus structures, including a memory bus or memory controller, a peripheral bus, an accelerated graphics port, and a processor or local bus using any of a variety of bus architectures. Bus 617 includes wired and/or wireless buses.

Memory/storage component 615 represents one or more computer storage media. Memory/storage component 615 includes volatile media (such as random access memory (RAM)) and/or nonvolatile media (such as read only memory (ROM), flash memory, optical disks, magnetic disks, and so forth). Memory/storage component 615 includes fixed media (e.g., RAM, ROM, a fixed hard drive, etc.) as well as removable media (e.g., a Flash memory drive, a removable hard drive, an optical disk, and so forth).

One or more I/O devices 616 allow a customer, utility, or other user to enter commands and information to computing device 618, and also allow information to be presented to the customer, utility, or other user and/or other components or devices. Examples of input devices include, but are not limited to, a keyboard, a cursor control device (e.g., a mouse), a microphone, a touchscreen, and a scanner. Examples of output devices include, but are not limited to, a display device (e.g., a monitor or projector), speakers, outputs to a lighting network (e.g., DMX card), a printer, and a network card.

Various techniques are described herein in the general context of software or program modules. Generally, software includes routines, programs, objects, components, data structures, and so forth that perform particular tasks or implement particular abstract data types. An implementation of these modules and techniques are stored on or transmitted across some form of computer readable media. Computer readable media is any available non-transitory medium or non-transitory media that is accessible by a computing device. By way of example, and not limitation, computer readable media includes "computer storage media".

"Computer storage media" and "computer readable medium" include volatile and non-volatile, removable and non-removable media implemented in any method or technology for storage of information such as computer readable instructions, data structures, program modules, or other data. Computer storage media include, but are not limited to, computer recordable media such as RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which is used to store the desired information and which is accessible by a computer.

The computer device 618 is connected to a network (not shown) (e.g., a LAN, a WAN such as the Internet, cloud, or any other similar type of network) via a network interface connection (not shown) according to some example embodiments. Those skilled in the art will appreciate that many different types of computer systems exist (e.g., desktop computer, a laptop computer, a personal media device, a mobile device, such as a cell phone or personal digital assistant, or any other computing system capable of executing computer readable instructions), and the aforementioned input and output means take other forms, now known or later developed, in other example embodiments. Generally speaking, the computer system 618 includes at least the minimal processing, input, and/or output means necessary to practice one or more embodiments.

Further, those skilled in the art will appreciate that one or more elements of the aforementioned computer device 618 is located at a remote location and connected to the other elements over a network in certain example embodiments. Further, one or more embodiments is implemented on a distributed system having one or more nodes, where each portion of the implementation (e.g., control engine 406, control engine 506) is located on a different node within the distributed system. In one or more embodiments, the node corresponds to a computer system. Alternatively, the node corresponds to a processor with associated physical memory in some example embodiments. The node alternatively corresponds to a processor with shared memory and/or resources in some example embodiments.

Figure 7:
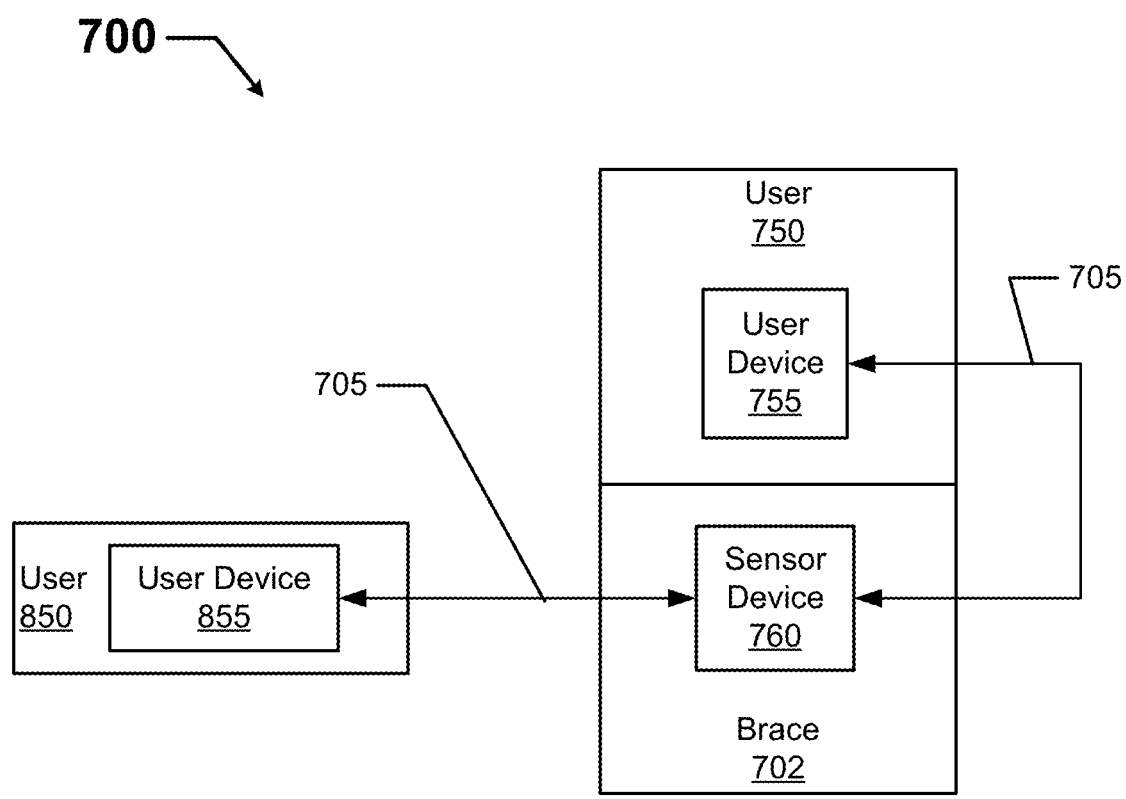
FIG. 7 shows a block diagram of a system according to certain example embodiments.

FIG. 7 shows a block diagram of a system 700 according to certain example embodiments. Referring to FIGS. 1 through 7, the system 700 of FIG. 7 includes a first user 750 (e.g., a child with clubfoot) wearing an example brace 702 that includes a sensor device 760. The system 700 of FIG. 7 can also include a second user 850 (e.g., a physician). The sensor device 760 communicates with the user device 755 of user 750 using communication links 705. The sensor device 760 also communicates with the user device 855 of user 850 using communication links 705. The components (or portions thereof) of the system 700 of FIG. 7 can be substantially the same as the corresponding components (or portions thereof) of the system 400 of FIG. 4 or the system 500 of FIG. 5.

In this case, the brace 702 can be similar to the brace 102 of FIG. 1, so that the user 750 can "walk" (move while upright) while wearing the brace 702. In this way, one or more sensors of the sensor device 760 of the brace 702 can measure one or more parameters related to movement of the brace 702 while the user 750 is wearing the brace 702. The controller of the sensor device 760 can then calculate, using the parameters measured by the sensor device 760, the how many "steps" the user 750 has taken for a period of time (also measured by the timer of the controller of the sensor device 760).

At the same time, one or more sensors of the sensor device 760 of the brace 702 can measure an amount of pressure in the foot restraints of the brace 702, which can be equated by the controller of the sensor device 760 to the feet of the user 750 being placed in the foot restraints for a period of time. This information can be communicated to the user device 855 of the user 850 so that the user 850 knows how often and for how long the user 750 is wearing the brace 702. The information communicated by the sensor device 760 to the user device 755 and/or the user device 855 can be provided periodically, in real time, on demand, or on some other basis.

User device 755 and user device 855 can each have an application (also called an app) loaded thereon. In such a case, the app can be used to present the information provided by the controller of the sensor device 760. The app can also allow user 750 and/or user 850 to organize and format the information provided by the controller of the sensor device 760. In this example, when the app is loaded on both the user device 755 and the user device 855, communication between user 750 and user 850 can be directly facilitated through the app. For example, if user 750 is wearing the brace 702 in the manner prescribed by user 850, then user 850 can send a message of encouragement to user 750 through the app. In addition, or in the alternative, the app can automatically post communications (e.g., "You are a bit behind schedule. Please wear the brace for another hour today." "Great job in wearing your brace today!") on the user device 755 based on settings and threshold values loaded into the app.

In certain example embodiments, the brace 702 can include one or more audio components (e.g., a speaker) that allows direct communication between the user 750 and the brace 702 without the need of a user device 755 or an app on the user device 755. In such a case, the controller of the brace 702 can broadcast communications, such as those listed above, as an appropriate response to measurements received from the sensor device 760 and evaluated by the controller.

Figure 8A:
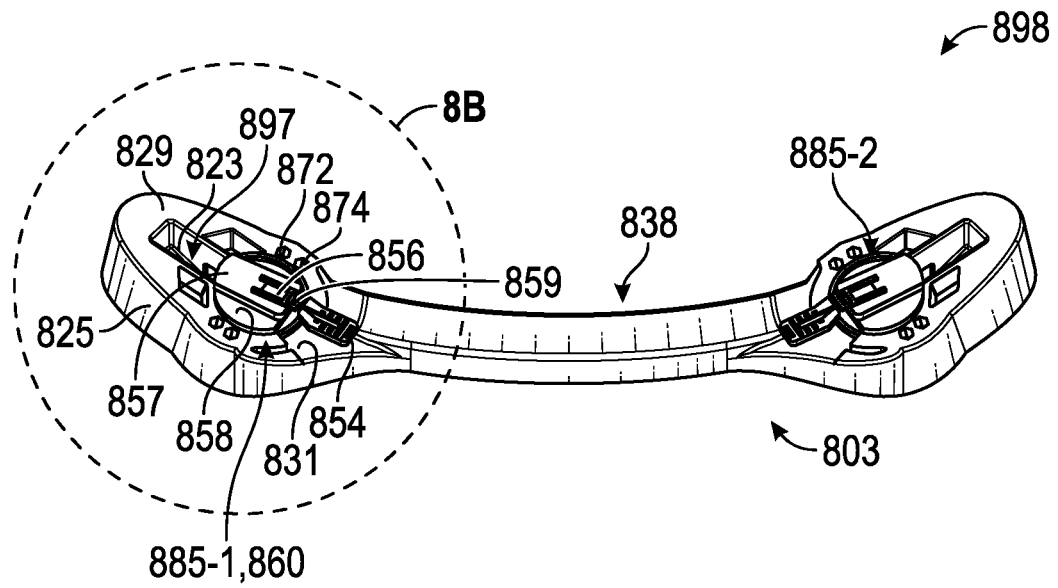
FIGS. 8A and 8B show a subassembly of a brace with a removable portion according to certain example embodiments.
Figure 8B:
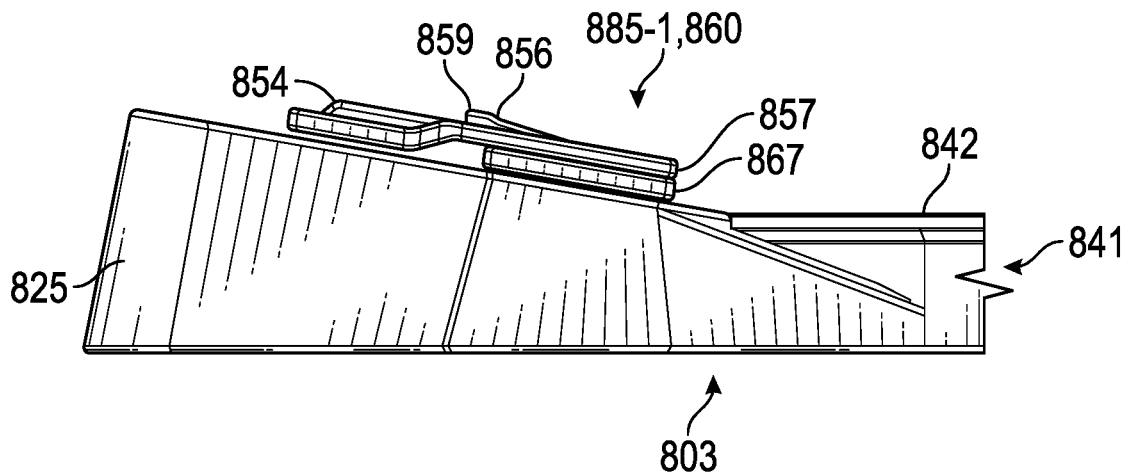
Figure 9A:
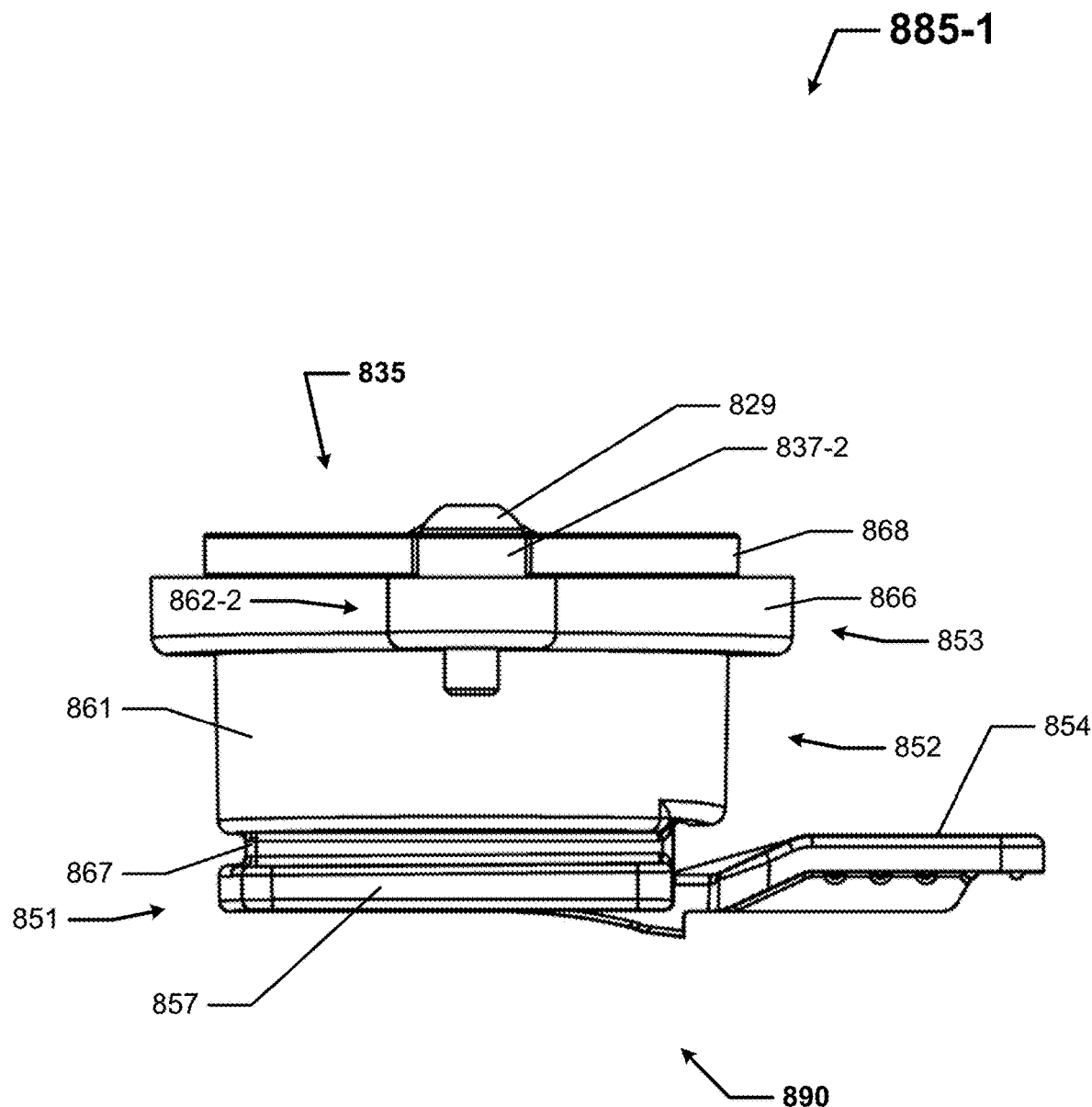
FIGS. 9A through 9E show various views of a sensor device integrated with a removable portion of the brace of FIGS. 8A and 8B.
Figure 9B:
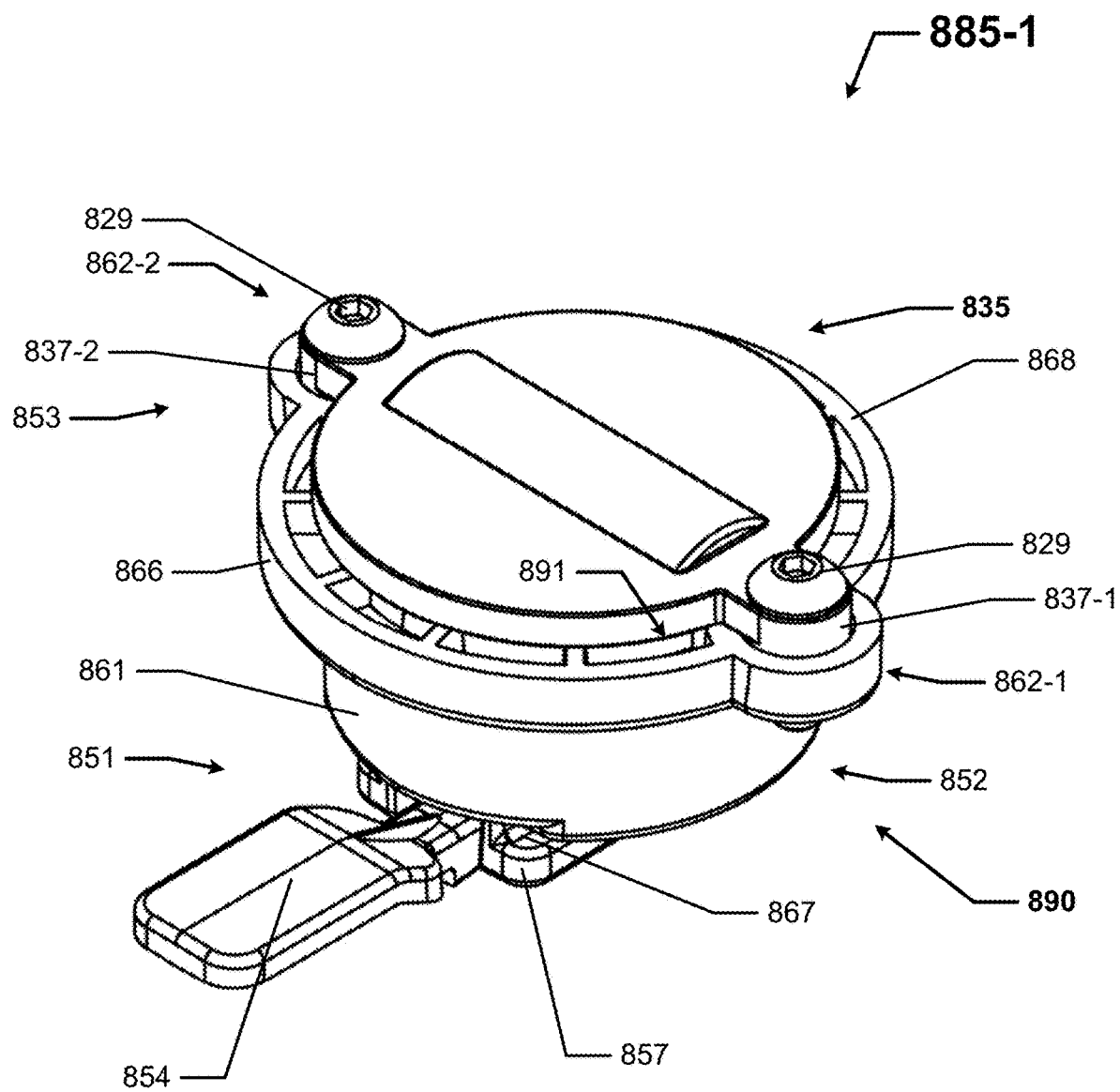
Figure 9C:
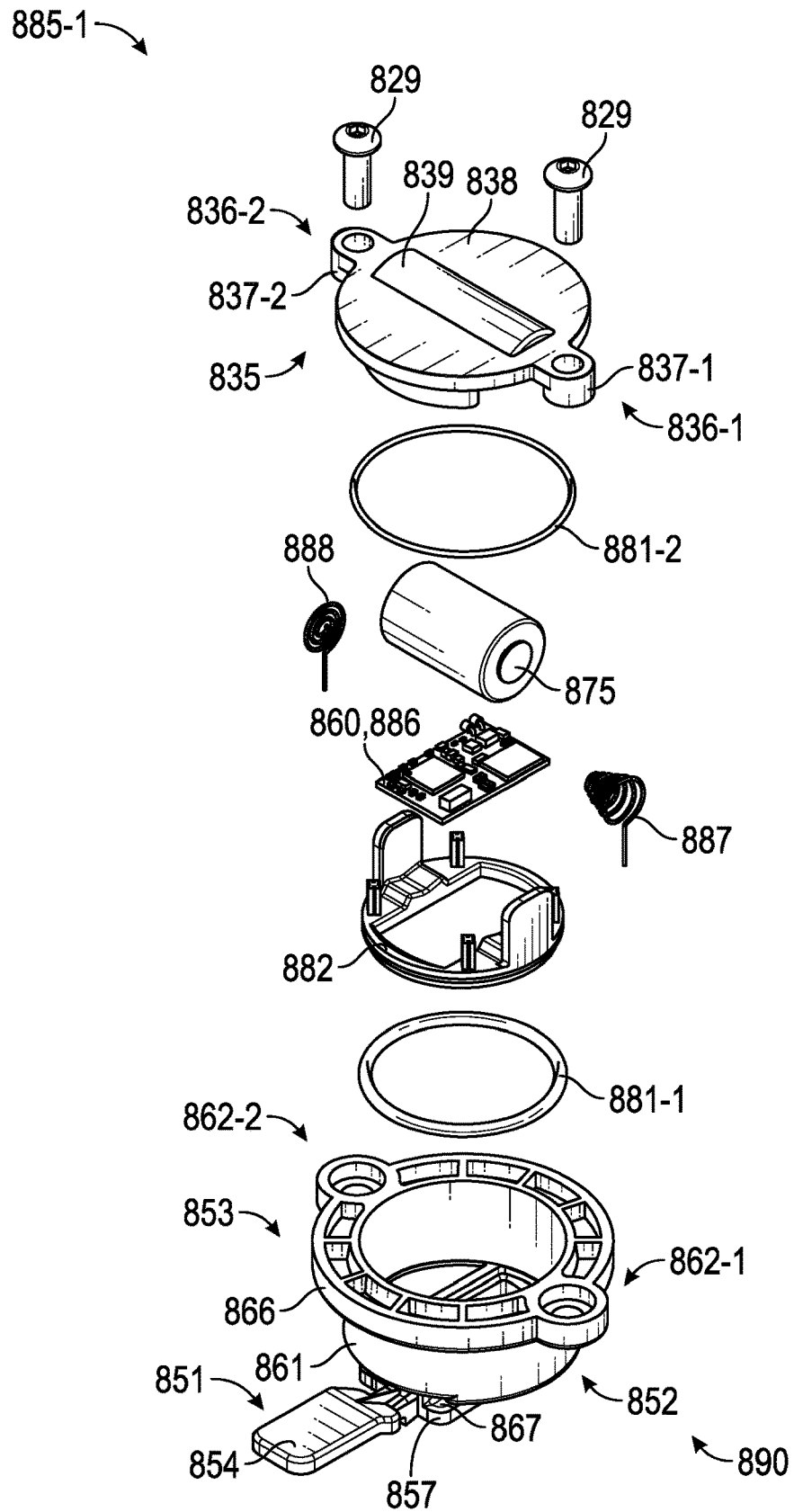
Figure 9D:
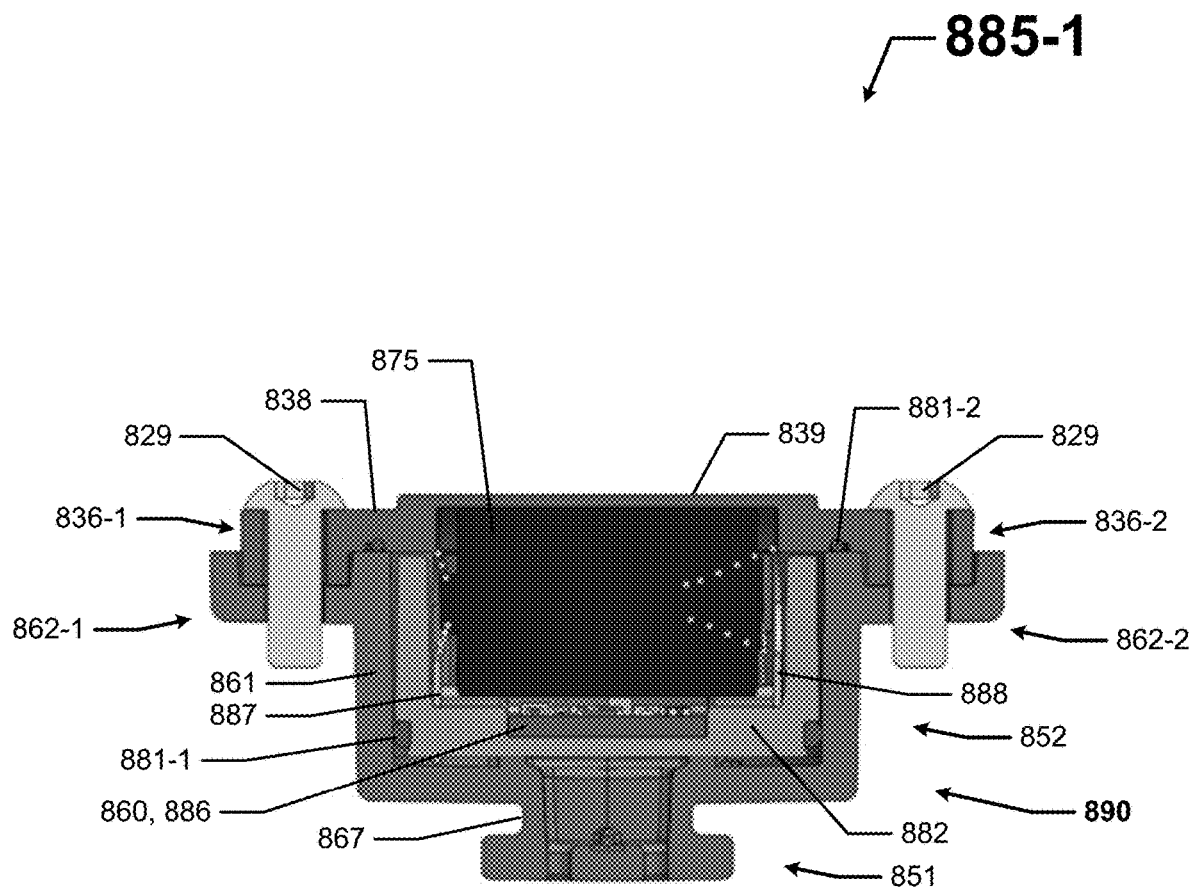
Figure 9E:
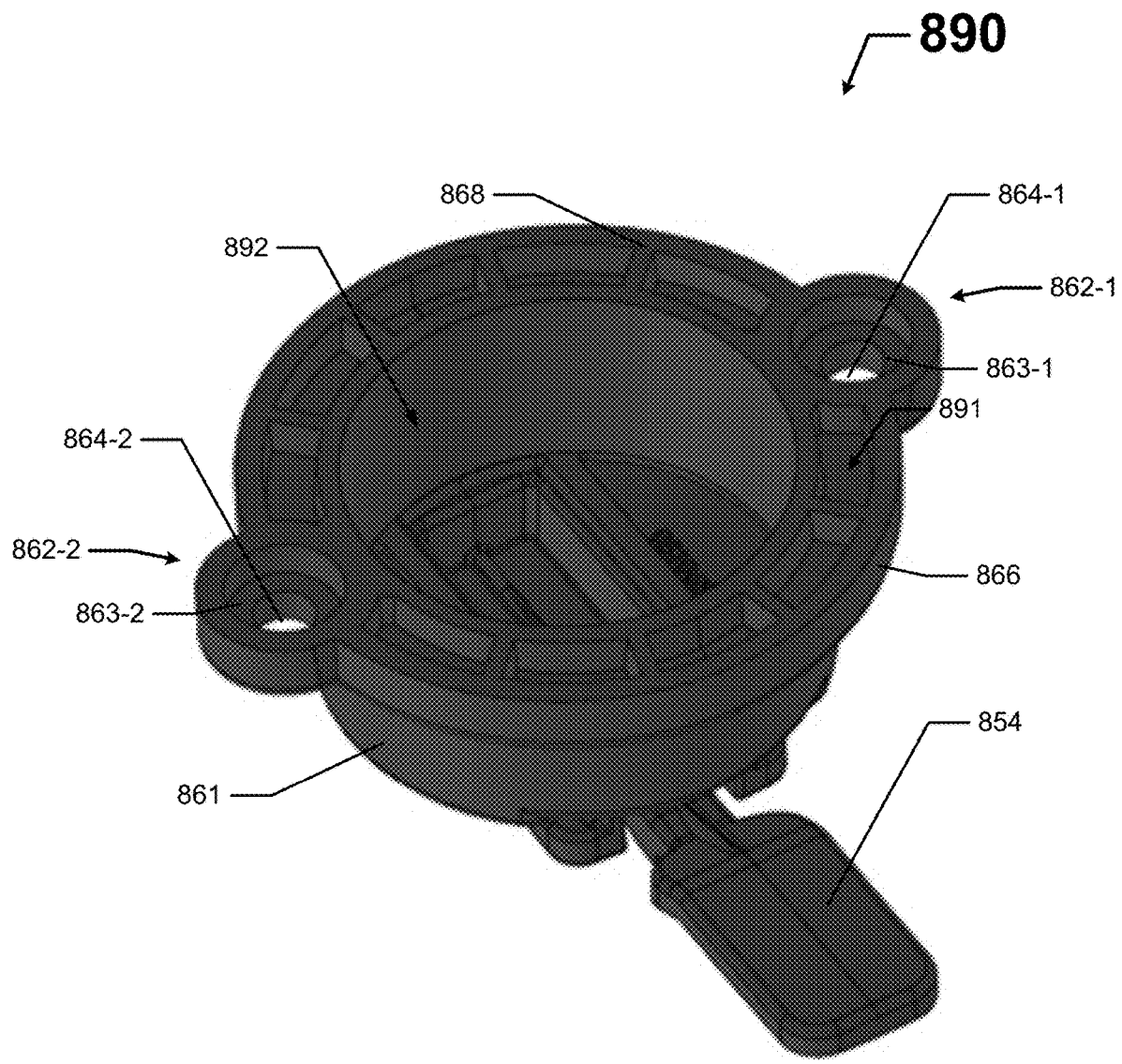

FIGS. 8A and 8B show a subassembly 898 of a brace with a removable portion according to certain example embodiments. Specifically, FIG. 8A shows a top perspective view of the subassembly 898, and FIG. 8B shows a side view of a detail of the subassembly 898. Also, FIGS. 9A through 9E show various views of a sensor device integrated with a removable portion of the brace of FIGS. 8A and 8B. Specifically, FIG. 9A shows a side view of the removable component 885-1 of the subassembly 898 of FIGS. 8A and 8B. FIG. 9B shows a bottom perspective view of the removable component 885-1 of the subassembly 898 of FIGS. 8A and 8B. FIG. 9C shows an exploded view of the subassembly 898 of FIGS. 8A and 8B. FIG. 9D shows a sectional side view of the subassembly 898 of FIGS. 8A and 8B. FIG. 9E shows a bottom perspective view of the body 890 of the removeable component 885-1 of FIGS. 8A and 8B. In FIGS. 9A through 9E, the removable component 885-1, which includes a sensor device 860, is inverted relative to what is shown in FIGS. 8A and 8B.

Referring to FIGS. 1 through 9E, the subassembly 898 of the brace includes a body 803 having two removable components 885 (specifically, removable component 885-1 and removable component 885-2). The subassembly 898 also has a single sensor device 860 that is disposed within the removable component 885-1. Aside from the sensor device 860, the subassembly 898 is substantially similar to a brace described in U.S. Pat. No. 10,314,730 issued on Jun. 11, 2019, which is hereby incorporated by reference herein. Those of ordinary skill in the art will appreciate that any of a number of other braces used for similar purposes (e.g., the treatment of clubfoot) can be modified according to example embodiments. In this example, the removable components 885 of the brace exist with or without the sensor device 860. In alternative embodiments, the body of a brace without a removable component can be modified to include one or more removable components for the purpose of facilitating one or more sensor devices.

The removable component 885-1 (referred to as a locking hub in U.S. Pat. No. 10,314,730) of FIGS. 8A through 9E includes a body 890 and a cover 835 coupled to the body 890. The body 890 and the cover 835 can be directly or indirectly coupled to each other. When the body 890 and the cover 835 are indirectly coupled to each other, one or more independent coupling features (e.g., a screw, a bolt, a rivet) can be used. Also, the body 890 and the cover 835 can be fixedly or detachably coupled to each other. In this example, the body 890 and the cover 835 are indirectly and detachably coupled to each other using two independent coupling features in the form of hex-head screws.

The body 890 of the removable component 885-1 in this case includes a coupling feature 851, a base 853, and an intermediate section 852. In certain example embodiments, the coupling feature 851 includes one or more mechanisms that mechanically couple (or decouple) the removable component 885-1 with a footplate or other component of the brace. For example, as shown in FIGS. 8A through 9E, the coupling feature 851 can include a slotted tongue 857, a stop 859 that is connected to a slotted tongue 857 by a ramp 856, and a tab 854 that is mechanically coupled to the stop 859.

The slotted tongue 857 can have a shape and size that allows the removable component 885-1 to moveably (e.g., slidably) couple to a footplate or other component of the brace. For example, as shown in FIGS. 8A through 9E, the slotted tongue 857 can be mounted on a base 867, where the slotted tongue 857 extends outward (laterally) beyond the base 867 at the front and both sides. In other words, when viewed from above, the base 867 cannot be seen because the outer sides of the slotted tongue 857 extend laterally beyond the base 867. The ramp 856 can be coupled to the slotted tongue 857 in such a way that the stop 859 and the ramp 856 are able to move in a vertical direction relative to and independently of the slotted tongue 857. This allows the stop 859 to slide into a certain position relative to a footplate (or other component of the brace) and mechanically couple to a corresponding receiving feature of the footplate (or other component of the brace).

The tab 854 can be depressed to move the stop 859 and at least the adjacent part of the ramp 856 vertically downward, which releases the stop 859 from a complementary coupling feature of a footplate (or other component of the brace), allowing the footplate (or other component of the brace) to decouple (e.g., slide) from the body 890 of the removable component 885-1 using the slotted tongue 857. In other words, by pressing the tab 854, a footplate (or other component of the brace) can decouple from the coupling feature 851 of the body 890 of the removable component 885-1 in reverse of how the footplate (or other component of the brace) couples to the coupling feature 851 of the body 890 of the removable component 885-1.

The shape and size of the tab 854 can be such that the tab 854 can fit within the extended section 823 of the keyhole 897. Specifically, the shape and size of the tab 854 can allow the tab 854 to traverse the extended section 823 of the keyhole 897. In certain example embodiments, the intermediate section 852 of the body 890 of the removable component 885-1 is positioned between the base 853 and the coupling feature 851. The intermediate section 852 can be shaped substantially the same as a core section of the keyhole 897 and can be disposed within the core section of the keyhole 897 when the coupling feature 851 of the body 890 of the removable component 885-1 is mechanically coupled to a footplate or other component of the brace. Further, the size of the intermediate section 852 can be less than (e.g., slightly less than, substantially less than) the size of the core section of the keyhole 897.

In addition, the intermediate section 852 can rotate while disposed within the core section of the keyhole 897. In such a case, the shape of the intermediate section 852 and the shape of the core section of the keyhole 897 can be substantially round when viewed from above. Further, in order for the coupling feature 851 to fit through the keyhole 897 to allow the intermediate section 852 to be disposed within the keyhole 897, the slotted tongue 857, the ramp 856, and the stop 859 can be contained within a vertical extension of the outer perimeter of the intermediate section 852. For example, when viewed from above, the slotted tongue 857, the ramp 856, and the stop 859 do not extend laterally beyond (when viewed from above) the outer edge (as denoted by side wall 861) of the intermediate section 852.

On the other hand, because of the extended section 823 of the keyhole 897, as well as the shape and size of the extended section 823, the tab 854 of the coupling feature 851 can extend laterally beyond (when viewed from above) the vertical extension of the side wall 861 of the intermediate section 852. When the removable component 885-1 is properly positioned within the keyhole 897, such that the intermediate section 852 of the body 890 is positioned within the central portion of the keyhole 897, the coupling feature 851 is positioned above the keyhole 897, which allows the coupling feature 851 to mechanically couple to a footplate or other component of the brace.

The base 853 of the body 890 of the removable component 885-1 can have a size (when viewed from above) that is larger than the size of the intermediate section 852. Thus, when the intermediate section 852 is disposed within the central portion of the keyhole 897, the top surface of the base 853 can abut against the bottom side of the body 803 of the brace and prevent the body 890 of the removable component 885-1 from traversing further upward through the keyhole 897. The base 853 of the body 890 of the removable component 885-1 can have a thickness around its perimeter (as shown by side wall 866) that can vary.

In certain example embodiments, the base 853 includes one or more of a number of coupling features 862. In this case, the base 853 of the body 890 of the removable component 885-1 includes coupling feature 862-1 and coupling feature 862-2. The coupling features 862 of the body 890 can be used to couple, directly or indirectly, the removable component 885-1 with one or more other components of the brace. In this example, the coupling features 862 can be used to couple the body 890 of the removable component 885-1 to the body 803 of the brace to set an abduction angle. In this example, the coupling feature 862-1 and the coupling features 862-2 are substantially identical to each other, where each coupling feature 862 includes an extension 863 (extension 863-1 corresponding to coupling feature 862-1, and extension 837-2 corresponding to coupling feature 862-2) disposed on opposite sides of the base 853 from each other and extending outward from the side wall 866 of the base 853. Each of the extensions 863 can have a height that is substantially similar to the height of the side wall 866. Each coupling feature 862 in this case also includes an aperture 864 that traverses the entire height of the extension 863.

In certain example embodiments, each coupling feature 862 (also called an abduction angle feature 862) of the base 853 of the body 890 of the removable component 885-1 can align with an abduction angle feature (e.g., abduction angle feature 872, abduction angle feature 874) disposed on the body 803 adjacent to the keyhole 897. If there are multiple abduction angle features 862 disposed on the base 853 of the removable component 885-1, each abduction angle feature 862 can be disposed in such a way as to align with multiple abduction angle features disposed on the body 803 of the brace. Alternatively, if there are multiple abduction angle features 862 disposed on the base 853 of the body 890 of the removable component 885-1, the abduction angle features 862 can be aligned with a single set of abduction angle features disposed on the body 803.

As mentioned above, the body 890 of the removable component 885-1 mechanically couples to the body 803 of the brace using one or more coupling features 862. Specifically, one or more abduction angle features 862 of the base 853 of the body 890 of the removable component 885-1 can be mechanically coupled to one or more abduction angle features (e.g., abduction angle feature 872, abduction angle feature 874) disposed on the body 803 of the brace adjacent to the keyhole 897. The abduction angle feature 862 of the body 890 of the removable component 885-1 can directly or indirectly couple to an abduction angle feature disposed on the body 803 of the brace. In this example, the abduction angle features 862 of the body 890 of the removable component 885-1 are indirectly coupled to the opposing abduction angle features 872 disposed on the body 803 of the brace using fastening devices (e.g., a bolt, a screw, a nut), which are hidden from view in FIGS. 8A and 8B.

In any case, when the abduction angle features 862 of the body 890 of the removable component 885-1 align with and couple to the abduction angle features disposed the body 803 adjacent to the keyhole 897, an abduction angle of the footplate, when coupled to the coupling feature 851 of the body 890 of the removable component 885-1, is set. The intermediate section 852 and the coupling feature 851 are held in a fixed position when the body 890 of the removable component 885-1 is coupled to the body 803 using the abduction angle features 862 of the body 890 of the removable component 885-1. In certain example embodiments, each abduction angle feature 862 is recessed so that a fastening device disposed in the abduction angle feature 862 is not damaged or otherwise compromised by normal use (e.g., standing, movement) of the brace.

In some cases, the coupling features (e.g., screws, bolts, nuts) used to couple the removable component 885-1 to the body 803 can only be done and undone using a tool (e.g., a screwdriver, a wrench). In other cases, the coupling features (e.g., rivets) used to couple the body 890 of the removable component 885-1 to the body 803 of the brace are tamperproof, and so cannot be undone without employing a destructive method.

The bottom surface 868 of the base 853 of the removable component 885-1 can be substantially planar. In certain example embodiments, a number of relief areas 891 are disposed within the bottom surface 868 of the body 890 to add strength to the removable component 885-1. The height of the base 853 (corresponding to the height of the side wall 866) of the body 890 can be no greater than the height of the side 825 of the body 803 of the brace adjacent to where the body 890 of the removable component 885-1 is positioned when coupled to the body 803 of the brace. In such a case, the body 890 of the removable component 885-1 is raised above the level formed by the bottom surface of the body 803 of the brace.

As discussed above, the body 803 of the subassembly 898 of the brace can include one or more of a number of features. For example, in this case, the body 803 includes a keyhole 897 (partially hidden from view in FIGS. 8A and 8B), an aperture, or other type of recess into which the removable component 885-1 can be disposed. In this case, the removable component 885-1 is initially inserted into and raised through the keyhole 897. Specifically, the tab 854 of the body 890 can be raised through the extended section 823 of the keyhole 897, while the remainder of the removable component 885-1 is raised through the core section of the keyhole 897.

In certain example embodiments, the shape of the tab 854 (e.g., rectangular, triangular) from a top view is substantially the same as, or different than, the shape of the extended section 823 of the keyhole 897. Similarly, the size of the tab 854 from a top view from any particular dimension (across, top to bottom) is less than the size of the extended section 823 of the keyhole 897 in a corresponding dimension. Alternatively, the extended section 823 of the keyhole 897 can be shorter than the tab 854. In such a case, the tab 854 (and, thus, the rest of the removable component 885-1) can be inserted through the extended section 823 (and, thus, the keyhole 897) at an angle.

The coupling feature 851 of the body 890 of the removable component 885-1 can be raised until the top surface 865 of the base 853 abuts against one or more features of the body 803 of the brace. For example, in this case, the coupling feature 851 can be raised until the coupling features 862 of the body 890 of the removable component 885-1 abut against the set of abduction angle features 872 disposed in the body 803 of the brace adjacent to the keyhole 897. In such a case, the intermediate section 852 of the body 890 of the removable component 885-1 is disposed within the core section of the keyhole 897.

When the intermediate section 852 of the body 890 of the removable component 885-1 is disposed within the core section of the keyhole 897, then the coupling feature 851 of the body 890 sits above the top 829 of the body 803 of the brace. Further, because the intermediate section 852 of the body 890 and the core section of the keyhole 897 have substantially the same shape (in this case, cylindrical) and size (e.g., height), with the outer perimeter of the intermediate section 852 being slightly smaller than the inner perimeter of the core section of the keyhole 897, the removable component 855-1 can rotate when disposed within the core section of the keyhole 897. Rotating the removable component 855-1 when the intermediate section 852 of the body 890 is disposed within the core section of the keyhole 897 is important to set the proper abduction angle for the brace.

In certain example embodiments, one or more features can be disposed on the top surface of body 803 of the brace to control the rotational movement of the removable component 855-1 when the removable component 855-1 is disposed within the core section of the keyhole 897. For example, a protrusion can extend upward from a portion of the body 803 of the brace where the recessed area 830 transitions to the top 842 of the crossbar 838. In such a case, the protrusion (e.g., an extension of the side wall 841 of the crossbar 838) can act as a stop against the tab 854 to prevent the removable component 855-1 from rotating to a certain position or beyond a certain point.

As discussed above, in this example, the sensor device 860 is disposed within a cavity 892 formed by the body 890 of the removable component 855-1. The sensor device 860 is integrated with a circuit board 886. Also disposed within the cavity 892 formed by the body 890 of the removable component 855-1 are an energy storage device 875 (in this case in the form of a battery), a platform 882, electrical terminal 887, electrical terminal 888, and two sealing members 881 (sealing member 881-1 and sealing member 881-2).

The electrical terminal 887 is coupled to one part of the circuit board 886 and makes contact with one end of the energy storage device 875, and the electrical terminal 888 is coupled to one part of the circuit board 886 and makes contact with the opposite end of the energy storage device 875. Under this configuration, the energy storage device 875 provides power to the components of the circuit board 886 (including the sensor device 860), through the electrical terminal 887 and the electrical terminal 888.

The platform 882 is configured to receive the circuit board 886, the energy storage device 875, the electrical terminal 887, and the electrical terminal 888 and to place those components in a particular orientation with respect to each other. The sealing member 881-1 is disposed in a channel at the bottom of the platform 882 and is configured to create a seal to prevent elements (e.g., dust, moisture) from outside the cavity 892 from entering the cavity 892 through a junction formed by the body 890 of the removable component 885-1 and the platform 882. The sealing member 881-2 is disposed in a channel at the bottom of the cover 835 and is configured to create a seal to prevent elements (e.g., dust, moisture) from outside the cavity 892 from entering the cavity 892 through a junction formed between the body 890 and the cover 835 of the removable component 885-1.

In certain example embodiments, the cover 835 includes one or more of a number of coupling features 836. In this case, the cover 835 of the removable component 885-1 includes coupling feature 836-1 and coupling feature 836-2. The coupling features 836 of the cover 835 can be used to couple, directly or indirectly, the cover 835 to the body 890 of the removable component 885-1, as well as to the body 803 of the brace to set an abduction angle. In this example, the coupling feature 836-1 and the coupling features 836-2 are substantially identical to each other, where each coupling feature 836 includes an extension 837 (extension 837-1 corresponding to coupling feature 836-1, and extension 837-2 corresponding to coupling feature 836-2) disposed on opposite sides of the cover 835 from each other and extending outward from the outer perimeter of the cover 835. Each of the coupling feature 836 in this case also includes an aperture that traverses the entire height of the extension 837.

The top surface 838 of the cover 835 can include a protrusion 839 to accommodate the shape of the energy storage device 875. In some cases, the optional protrusion 839 can be merely aesthetic without a functional purpose. In other cases, the optional protrusion 839 can have a functional purpose. For example, the protrusion 839 can be used to contact a charging station, docking port, or other similar device. In such a case, when the energy storage device 875 is rechargeable, the protrusion can facilitate charging the energy storage device 875.

Example embodiments use at least one sensor device to measure parameters that indicate movement and/or use of a brace. Example embodiments can also notify one or more users as to the movement and/or use of a brace. Example embodiments can work with any type of brace used to treat any of a number of conditions that affect any portion of a body, such as a brace used to treat clubfoot, a splint used to treat a sprained wrist, and a brace used to treat scoliosis. The sensor devices used with example embodiments can be operationally independent or integrated with a controller of a brace. Example embodiments can be used to monitor a single brace or multiple braces. Example embodiments provide a number of benefits. Such benefits can include, but are not limited to, more effective treatment using a brace, more timely notification of the movement and/or use of a brace, retrofitability with existing braces, ease of maintenance, and compliance with industry standards that apply to braces.

Although embodiments described herein are made with reference to example embodiments, it should be appreciated by those skilled in the art that various modifications are well within the scope and spirit of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. A foot abduction brace comprising:
   a body comprising two foot restraints and a crossbar disposed therebetween;
   a sensor device disposed inside of a removable component in one of the two foot restraints of the body, wherein the sensor device comprises a sensor that is configured to measure at least one parameter associated with a foot being disposed in the one of the two foot restraints, and wherein the sensor device is accessible from the removable component while the one of the two foot restraints is coupled to the removable component; and
   a controller communicably coupled to the sensor device, wherein the controller is configured to:
      receive a plurality of measurements of the at least one parameter taken by the sensor device; and
      determine, using the plurality of measurements, an amount of time within a time period that the foot is disposed in the one of the two foot restraints.

2. The foot abduction brace of claim 1, wherein the controller is further configured to determine, using the plurality of measurements, a number of steps that the body is used to take over the time period that the foot abduction brace is in use.

3. The foot abduction brace of claim 1, wherein the sensor device sends the plurality of measurements to the controller in real time.

4. The foot abduction brace of claim 1, wherein the body is further configured to treat clubfoot.

5. The foot abduction brace of claim 1, wherein the sensor of the sensor device comprises an accelerometer.

6. The foot abduction brace of claim 1, wherein the sensor of the sensor device comprises a gyroscope.

7. The foot abduction brace of claim 1, wherein the controller is further configured to send a notification as to the amount of time within the time period that the foot is disposed in the one of the two foot restraints.

8. The foot abduction brace of claim 1, further comprising:
   an additional sensor device disposed in a second of the two foot restraints of the body, wherein the additional sensor device comprises an additional sensor that is configured to measure the at least one parameter associated with an additional foot being disposed in the second of the two foot restraints,
   wherein the controller is further configured to receive a plurality of additional measurements of the at least one parameter taken by the additional sensor device, wherein the controller determines the amount of time within the time period that the foot and the additional foot disposed in the two foot restraints using the plurality of measurements and the plurality of additional measurements.

9. The foot abduction brace of claim 1, wherein the sensor device is disposed within a removable component of the one of the two foot restraints of the body.

10. The foot abduction brace of claim 9, wherein the removable component comprises an accessible cavity inside of which the sensor device is located, and wherein the removable component is configured to be removed in the absence of the sensor device in preparing the brace for use.

11. The foot abduction brace of claim 1, wherein the sensor device is inaccessible without use of a tool.

12. The foot abduction brace of claim 1, wherein the controller is further configured to:
   identify, after evaluating the plurality of measurements, a manner in which a user uses the brace.

13. The foot abduction brace of claim 1, wherein the controller comprises a transceiver for sending signals, wherein the signals comprise measurements made by the sensor device.

14. The foot abduction brace of claim 13, wherein the transceiver sends the signals to a user device.

15. The foot abduction brace of claim 14, wherein the signals comprise a report that communicates to a physician the amount of time within the time period that the foot is disposed in the one of the two foot restraints.

16. The foot abduction brace of claim 13, wherein the transceiver sends the signals to a network manager.

17. The foot abduction brace of claim 1, wherein the one of the two foot restraints is coupled to a coupling feature disposed at a top end of the removable component.

18. The foot abduction brace of claim 17, wherein the coupling feature comprises a stop and a slotted tongue mounted on a base.

19. The foot abduction brace of claim 17, wherein the coupling feature of the removable component further comprises a tab configured to release the one of the two foot restraints when depressed.

20. The foot abduction brace of claim 1, wherein the one of the two foot restraints is separable from the removable component while the removable component is coupled to the body.

* * * * *